US010385372B2

(12) United States Patent
Loria et al.

(10) Patent No.: US 10,385,372 B2
(45) Date of Patent: Aug. 20, 2019

(54) **METHODS FOR THAXTOMIN PRODUCTION AND MODIFIED STREPTOMYCES W

(56) References Cited

OTHER PUBLICATIONS

Guan, D., et al. 2012. Evidence that thaxtomin C is a pathogenicity determinant of Streptomyces ipomoeae, the causative agent of Streptomyces soil rot disease of sweet potato. Mol. Plant Microbe Interact. 25(3): 393-401.

Gust, B., et al. 2003. PCR-targeted Streptomyces gene replacement identifies a protein domain needed for biosynthesis of the sesquiterpene soil odor geosmin. Proc. Natl. Acad. Sci. U.S.A. 100: 1541-1546.

Hihard, S., et al. 2007. PREDetector: a new tool to identify regulatory elements in bacterial genomes. Biochem. Biophys. Res. Commun. 357(4): 861-864.

Heim, D.R., et al. 1990. Isoxaben inhibits synthesis of acid insoluble cell wall materials in *Arabidopsis thaliana*. Plant Physiol. 93: 695-700.

Hopwood, D.A. 2007. How do antibiotic-producing bacteria ensure their self-resistance before antibiotic biosynthesis Incapacitates them? Mol. Microbiol. 63(4): 937-940.

Johnson, E.G., Joshi, M.V., Gibson, D.M. and Loria, R. 2007. Cello-oligosaccharides released from host plants induce pathogenicity in scab-causing Streptomyces species. Physiol. Mol. Plant Pathol. 71: 18-25.

Johnson, E.G., et al. 2009. 4-Nitrotryptophan is a substrate for the non-ribosomal peptode synthetase TxtB in the thaxtomin A biosynthetic pathway. Mol. Microbiol. 73(3): 409-418.

Kieser, T., et al. 2000. Practical Streptomyces genetics. Norwich, UK, The John Innes Foundation, 1 page.

King, R.R., et al. 2001. Herbicidal properties of the thaxtomin group of phytotoxins. J. Agric. Food Chem. 49(5): 2298-2301.

Lauzier, A., et al. 2008. Effect of potato suberin on Streptomyces scabies proteome. Mol. Plant Pathol. 9(6): 753-762.

Loria, R., et al. 2008. Thaxtomin biosynthesis: the path to plant pathogenicity in the genus Streptomyces. Antonie van Leeuwenhoek 94(1): 3-10.

Loria, R., et al. 1995. Differential production of thaxtomins by pathogenic Streptomyces species in vitro. Biochem. Cell. Biol. 85(5): 537-541.

MacNeil, D., et al. 1992. Analysis of Streptomyces avermitilis genes required for avermectin biosynthesis utilizing a novel integration vector. Gene 111(1): 61-68.

Marushima, K., Ohnishi, Y. and Horinouchi, S. 2009. CebR as the master regulator for cellulose/cellooligosaccharide catabolism affects morphological development in Streptomyces griseus. J. Bacteriol. 191(19): 5930-5940.

Scheible, W.R., et al. 2003. An *Arabidopsis* mutant resistant to thaxtomin A, a cellulose synthesis inhibitor from Streptomyces scabies. Plant Cell 15(8): 1781-1794.

Schlösser, A., et al. 2000. Binding characteristics of CebR, the regulator of the ceb operon required for cellobiose/cellotriose uptake in Streptomyces reticuli. FEMS Microbiol. Lett. 190(1): 127-132.

Schlösser, A., et al. 1997. The Streptomyces ATP-binding component MsiK assists in cellobiose and maltose transport. J. Bacteriol. 179(6): 2092-2095.

Wach, M.J., et al. 2007. Effect of carbohydrates on the production of thaxtomin A by Streptomyces acidiscabies. Arch. Microbiol. 188(1): 81-88.

Loria, et al. Evolution of Plant Pathogenicity in Streptomyces, Annu Rev. Phytopathol.

Bignell, et al. Thaxtomin a Production and Virulence are Controlled by several bld Gene Global Regulators in Streptomyces scabies; Department of Biology, Memorial University of Newfoundland, St. John's, NLA18 3X9, Canada; Department of Plant Pathology, Institute of Food and Agricultural Sciences; 11 pages.

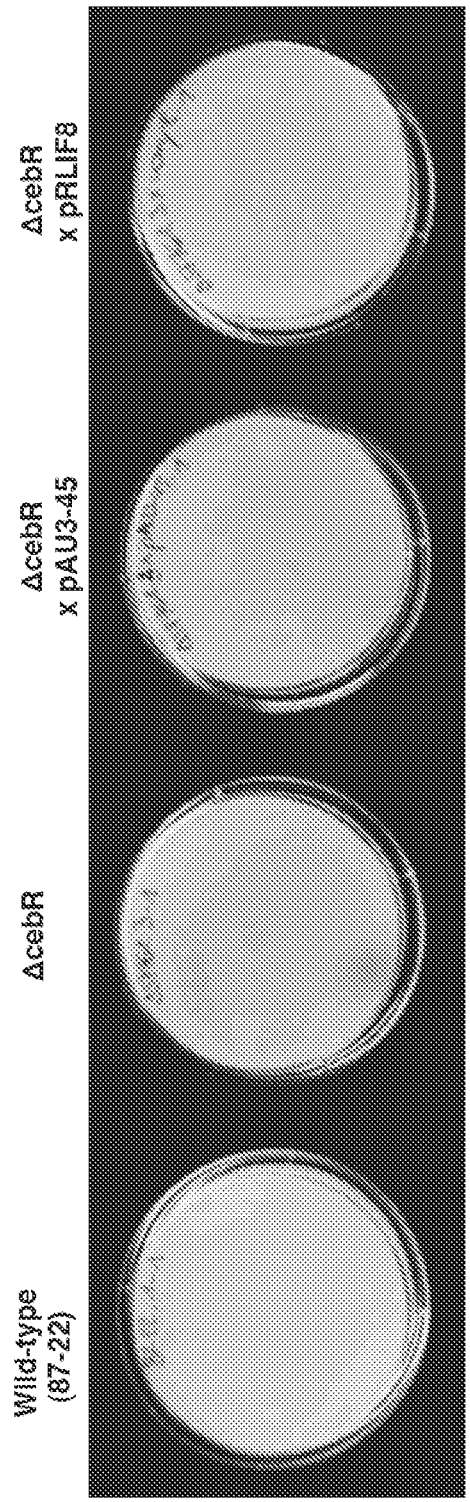
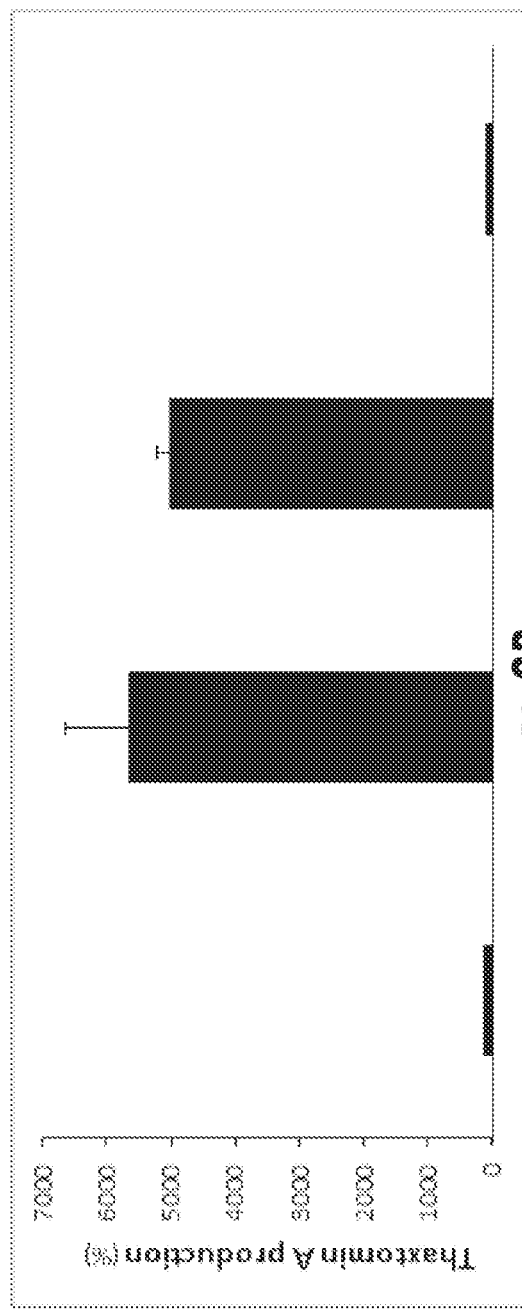
FIG. 8A
FIG. 8B

METHODS FOR THAXTOMIN PRODUCTION AND MODIFIED STREPTOMYCES WITH INCREASED THAXTOMIN PRODUCTION

CROSS-REFERENCE TO RELATED APPLICATIONS

This application is the 35 U.S.C. § 371 national stage application of PCT Application No. PCT/US2015/050582, filed Sep. 17, 2015, where the PCT claims the benefit of and priority to U.S. Provisional Application Ser. No. 62/052,681, having the title "METHODS FOR THAXTOMIN PRODUCTION AND MODIFIED *STREPTOMYCES* WITH INCREASED THAXTOMIN PRODUCTION", filed on Sep. 19, 2014, both of which are herein incorporated by reference in their entireties.

STATEMENT REGARDING FEDERALLY SPONSORED RESEARCH OR DEVELOPMENT

This invention was made with government support under Grant No. 2010-65110-20372 awarded by the USDA/NIFA. The government has certain rights in the invention.

SEQUENCE LISTING

This application contains a sequence listing filed in electronic form as an ASCII.txt file entitled 02276058.txt, created on Sep. 17, 2015, and having a size of 19900 bytes. The content of the sequence listing is incorporated herein in its entirety.

BACKGROUND

The thaxtomins are a group of phytotoxins generated by some species of *Streptomyces* bacteria, such as *Streptomyces scabies* (the main causal organism of potato common scab). The thaxtomins can cause plant cell necrosis of various plant species.

Five toxins, including thaxtomin A and thaxtomin B, that induce the formation of scabs on potato tubers have been isolated from *S. scabies*. They are cyclic dipeptides classed as 2,5-Diketopiperazines, with thaxtomin A, the most abundant, having the chemical formula $C_{22}H_{22}N_4O_6$. Individual thaxtomins appear to differ only in the presence or absence of N-methyl and hydroxyl groups and their respective substitution sites. For instance, thaxtomin A and thaxtomin B differ only in the presence of a hydrogen at $C_{20}$ in thaxtomin B, rather than a hydroxyl group.

The pathogenicity of *Streptomyces* strains is believed to be related to the amount of thaxtomin A they produce, as thaxtomin A is believed to be the most physiologically active. It is synthesized by peptide synthetases encoded by the txtA and txtB genes. The genes involved in thaxtomin biosynthesis are located on a part of the genome called the pathogenicity island, also present in *S. acidiscabies* and *S. turgidiscabies*.

Cellobiose and cellotriose, subunits of cellulose, activate thaxtomin production in some strains. The target of the thaxtomins is unknown, but evidence suggests that they inhibit the growth of plant cell walls, having an apparent ability to inhibit cellulose synthesis in developing plant cells. They are not organ- or plant-specific and cause death in various plant species.

Although studies have indicated that the thaxtomins have many of the biological properties desirable in a commercial herbicide, production on an industrial scale presents problems, such as slow production, low yields, and the need for certain inducers, such as cellobiose.

SUMMARY

In accordance with the purpose(s) of the present disclosure, as embodied and broadly described herein, embodiments of the present disclosure relate to genetically modified *Streptomyces* bacteria capable of increased thaxtomin production, genetically modified *Streptomyces* bacteria with reduced activity of a CebR protein encoded by a cebR gene and/or reduced activity of a β-glucosidase enzyme encoded by the bglC gene, genetically modified *Streptomyces* bacteria including a mutation of a native cebR gene and/or a native bglC gene, methods of increasing thaxtomin production in *Streptomyces* bacteria, methods of suppressing CebR and/or BglC activity, methods of producing thaxtomin, and thaxtomin produced by the methods of the present disclosure.

An embodiment of the present disclosure includes a genetically modified *Streptomyces* bacterium comprising a mutation that reduces activity of a CebR protein encoded by a cebR gene, such that the genetically modified *Streptomyces* has increased production of a thaxtomin compound as compared to a corresponding wild type *Streptomyces* bacterium.

An embodiment of the present disclosure also includes a genetically modified *Streptomyces* bacterium comprising a mutation that reduces activity of a β-glucosidase enzyme encoded by a bglC gene, such that the genetically modified *Streptomyces* has increased production of a thaxtomin compound as compared to a corresponding wild type *Streptomyces* bacterium.

An embodiment of the present disclosure includes a method of increasing production of a thaxtomin compound in a *Streptomyces* bacterium, the method comprising providing a *Streptomyces* bacterium from a species capable of producing one or more thaxtomin compounds under standard thaxtomin-inducing conditions and genetically modifying the *Streptomyces* bacterium by creating a mutation in the bacterium, wherein the mutation reduces activity of a CebR protein encoded by a cebR gene, such that the genetically modified *Streptomyces* has increased production of a thaxtomin compound as compared to a corresponding wild type *Streptomyces* bacterium.

An embodiment of the present disclosure includes a method of increasing production of a thaxtomin compound in a *Streptomyces* bacterium, the method comprising providing a *Streptomyces* bacterium from a species capable of producing one or more thaxtomin compounds under standard thaxtomin-inducing conditions, and genetically modifying the *Streptomyces* bacterium by creating a mutation in the bacterium, wherein the mutation reduces activity of a β-glucosidase enzyme encoded by a bglC gene, such that the genetically modified *Streptomyces* has increased production of a thaxtomin compound as compared to a corresponding wild type *Streptomyces* bacterium.

An embodiment of the present disclosure includes a method of increasing production of a thaxtomin compound in a *Streptomyces* bacterium, the method comprising suppressing the activity of one or more of the group selected from a CebR protein encoded by a cebR gene or a β-glucosidase enzyme encoded by a bglC gene.

An embodiment of the present disclosure includes a method of producing a thaxtomin compound, the method comprising culturing genetically modified *Streptomyces* bacteria, wherein the genetically modified *Streptomyces* bacteria have a mutation selected from at least one of a mutation of a native cebR gene and a mutation of a native bglC gene, wherein the mutation reduces production or functionality of at least one of a CebR repressor encoded by the cebR gene and a β-glucosidase enzyme encoded by the bglC gene, such that the modified *Streptomyces* bacteria have increased production of a thaxtomin compound as compared to a corresponding wild type *Streptomyces* bacteria.

Other genetically modified strains of bacteria, methods, features, and advantages will be or become apparent to one with skill in the art upon examination of the following drawings and detailed description. It is intended that all such additional genetically modified strains of bacteria, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A is an image of *Streptomyces scabies*, FIG. 1B shows potato scab lesions caused by *Streptomyces scabies*, and FIG. 1C shows the structure of thaxtomin A.

FIG. 7A illustrates an analysis of growth conditions showing that deletion of cebR in *S. scabies* resulted in higher thaxtomin production (determined by intensity of pigmentation, as graphed in FIG. 7B) on OBA and even in production under conditions which do not trigger thaxtomin production in the wild type strain 87-22. FIG. 7B is a graphic representation of HPLC analysis of thaxtomin A extracted from the plates shown in FIG. 7A.

FIGS. 8A-B illustrate genetic complementation of the cebR mutant scored by thaxtomin production on ISP-4 plates. FIG. 8A is a digital image of a visual inspection of ISP-4 plates, where thaxtomin production is displayed by typical yellow pigmentation. Although pigmentation is not visible in the black and white photos, FIG. 8B is a graphic illustration HPLC analysis of thaxtomin production on the ISP-4 plates from FIG. 8A. The cebR mutant (and the cebR mutant transformed with the empty pAU3-45 plasmid as a negative control for the complementation) produce thaxtomin under conditions that do not induce toxin production in the wild-type strain. Thaxtomin production is reverted back to wild-type levels when the mutation is genetically complemented (cebR mutant transformed with pRLIF8 containing the cebR gene and its promoter region).

DETAILED DESCRIPTION

Figure 1A:
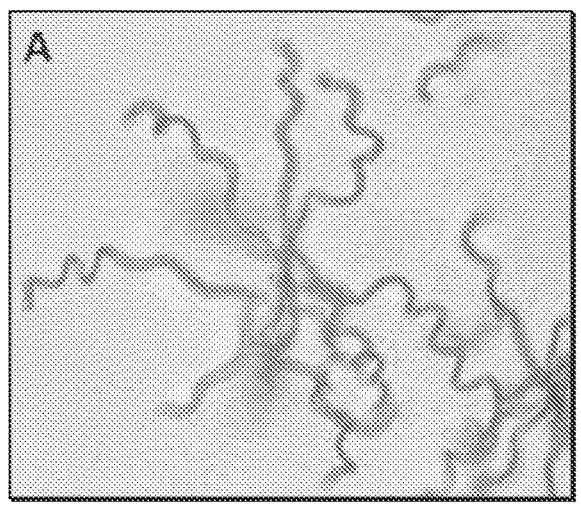
FIGS. 1A-C illustrate *Streptomyces scabies* and thaxtomin A.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, botany, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to double-stranded regions comprising RNA or DNA or both RNA and DNA. The strands in such regions may be from the same molecule or from different molecules. The regions may include all of one or more of the molecules, but more typically involve only a region of some of the molecules. One of the molecules of a double-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence. As used herein, a "transgene" refers to an artificial gene or portion thereof that is used to transform a cell of an organism, such as a bacterium or a plant.

As used herein, "transgenic" refers to a cell, tissue, or organism that contains a transgene.

As used herein, "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

The term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments)), the combination of a nucleic acid encoding a polypeptide to a promoter sequence, where the coding sequence and promoter sequence are from different sources or otherwise do not typically occur together naturally). Recombinant also refers to the polypeptide encoded by the recombinant nucleic acid. Non-naturally occurring nucleic acids or polypeptides include nucleic acids and polypeptides modified by man.

As used herein, "isolated" means removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a CCD enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It can refer to transcription or the combination of transcription and translation. Expression generally refers to the transcription of a gene to produce messenger RNA, as used herein expression may refer to the entire process of "expression" of a nucleic acid to produce a polypeptide (e.g., transcription plus translation). If "expression" is used in reference to a polypeptide, it indicates that the polypeptide is being produced via expression of the corresponding nucleic acid.

As used herein, the term "over-expression" and "up-regulation" or "increasing" production of a polypeptide refers to the expression of a nucleic acid encoding a polypeptide (e.g., a gene) in a modified cell at higher levels (therefore producing an increased amount of the polypeptide encoded by the gene) as compared to a "wild type" cell (e.g., a substantially equivalent cell that is not modified in the manner of the modified cell) under substantially similar conditions. Thus, to over-express or increase expression of thaxtomin refers to increasing or inducing the production of the thaxtomin dipeptide by one or more enzymes encoded by the thaxtomin biosynthetic genes, which may be done by a variety of approaches, such as, but not limited to: increasing the transcription of the genes (such as by placing the genes under the control of a constitutive promoter) responsible for synthesis of thaxtomin, or increasing the translation of such genes, inhibiting or eliminating a repressor of thaxtomin production (e.g., CebR or β-glucosidase enzyme), or a combination of these and/or other approaches.

Conversely, "under-expression" and "down-regulation" refers to expression of a polynucleotide (e.g., a gene) at lower levels (producing a decreased amount of the polypeptide encoded by the polynucleotide) than in a "wild type" cell. As with over-expression, under-expression can occur at different points in the expression pathway, such as by decreasing the number of gene copies encoding for the polypeptide; removing, interrupting, or inhibiting (e.g., decreasing or preventing) transcription and/or translation of the gene (e.g., by the use of antisense nucleotides, suppressors, knockouts, antagonists, etc.), or a combination of such approaches. "Suppression" refers to the inhibition of production and/or activity functional gene product. Thus, the suppression of a gene or protein may indicate that the expression of the gene and/or activity of the encoded peptide has been inhibited such as by transcription and/or translation being inhibited, thus resulting in low to no production of the encoded protein, or production of a non-functional product, or production of an interfering nucleic acid that otherwise suppresses activity of the target protein.

Similarly, with respect to a gene product, such as a protein, "reduced activity" indicates that the activity of the protein is reduced relative to activity in a "wild type cell". Such reduction in activity can be the result of inhibition/suppression/down-regulation/under-expression of the gene encoding the protein, the result of inhibition of translation of the messenger RNA into a functional gene product, or the result of production of a non-functional protein with reduced or no activity, or the direct suppression of the protein activity (e.g., preventing binding to a target), or the like. "Reduced production" of a gene product (e.g., a protein), such as by suppression, interruption, or other inhibition of transcription or translation, may result in reduced activity, but "reduced activity" of a protein or other gene product may result from other causes other than "reduced production", such as set for the above.

As used herein a "mutation" refers to a heritable change in genetic material, which may include alteration of single base pairs of a nucleic acid, or the deletion, insertion, or rearrangement of larger sections of genes or chromosomes. An "engineered mutation" refers to a mutation created by human design (e.g., the mutation did not spontaneously occur by natural causes and/or was the result of intentional human manipulation). A "genetically modified" organism is an organism whose genetic material has been altered by one or more engineered mutations (e.g., human induced mutations).

The term "null mutation" refers to a mutation in which the gene product (e.g., the protein encoded by the gene) is either not produced (or produced at significantly reduced levels, so as to be negligible) or is non-functional. Typically, a null mutation will involve a mutation of the native gene, such that the gene is not transcribed into RNA, the RNA product cannot be translated, or the protein produced by gene expression is non-functional.

The term "plasmid" as used herein refers to a non-chromosomal double-stranded DNA sequence including an intact "replicon" such that the plasmid is replicated in a host cell. A plasmid may include exogenous nucleic acid sequences and/or recombinant sequences.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. As such, expression vectors typically contain recombinant nucleic acid sequences having different sequences linked together to effect expression of a target sequence. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest (e.g., an exogenous nucleic acid sequence, a recombinant sequence, etc.), where the plasmid or expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *E. coli*), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest.

The terms "native," "wild type", or "unmodified" in reference to a polypeptide/protein/enzyme, polynucleotide, cell, or organism, are used herein to provide a reference point for a variant/mutant of a polypeptide/protein/enzyme, polynucleotide, cell, or organism prior to its mutation and/or modification (whether the mutation and/or modification occurred naturally or by human design).

As used herein, "thaxtomin" or "thaxtomin compound" refers to one or more compounds from a family of cyclic dipeptide phytotoxins, 4-nitroindol-3-yl-containing 2,5-dioxopiperazines, generated by some species of *Streptomyces* bacteria (and possibly by other actinomycetes) and exhibiting toxicity to various plant species. Thaxtomin compounds of the present disclosure have the general formula of Formula I below, and variants thereof. At least 5 thaxtomin compounds have been characterized, including thaxtomin A, A ortho analog, B, C, and D, and up to at least 12 different variants identified. Thaxtomin A, the most abundant of the thaxtomins and also believed to be the most physiologically active, has the chemical formula $C_{22}H_{22}N_4O_6$ (chemical structure illustrated in FIG. 1C). The thaxtomins can cause plant cell necrosis of various plant species and can induce the formation of scabs on potato tubers have been isolated from S, scabies. As used herein "thaxtomin" and "thaxtomin compound" refers generally to any of the members of this chemical group. Much of the discussion of thaxtomin in the present disclosure is in reference to thaxtomin A; however, as thaxtomin A may be a precursor to other thaxtomin compounds and/or the production of thaxtomin A is interwoven with production of other thaxtomin compound's, to the extend the methods and compositions of the present disclosure also modulate the production of other thaxtomin compounds, this is also intended to fall within the scope of the present disclosure. The general structure of a thaxtomin is shown below as Formula where R1 and R3 are independently selected from methyl or H and where R2, R4, R5, and R6 are each independently selected from hydroxyl or H.

Formula 1

The terms "thaxtomin-inducing conditions" indicates certain environmental conditions (e.g., natural or cell culture conditions) known to induce thaxtomin production in wild-type *Streptomyces* bacterial species known to be capable of thaxtomin production. For instance, wild type *Streptomyces* are induced to produce thaxtomin in the presence of certain products of cellulose degradation, such as, but not limited to, cellobiose, as well as xylan-degradation products (Wach et al. 2007), such as, but not limited to suberin (Lauzier et al. 2008). In embodiments, "thaxtomin-inducing conditions" may include specific conditions or cell culture media (such as but not limited to, Oat Bran Broth (OBB), Oat Bran Agar (OBA), etc.) known to induce thaxtomin production in cell culture of wild-type *Streptomyces* species (such as, but not limited to *S. scabies, S. acidiscabies*, and *S. turgidiscabies*). In embodiments, "thaxtomin-inducing conditions" may also include a standard cell culture growth medium supplemented with a known thaxtomin-inducing compound, such as, but not limited to cellobiose.

The term "cebR gene" as used in the present disclosure indicates a nucleic acid sequence encoding a CebR protein in a *Streptomyces* or other thaxtomin-producing *Actinomycete* species that is a modulator of thaxtomin production. In embodiments, "cebR genes" include the cebR gene of *S. scabies* (SEQ ID NO: 1) and variants and/or homologs (e.g., orthologs and paralogs) thereof retaining the function of modulation of thaxtomin production. In embodiments "cebR genes" include nucleic acids having a sequence of SEQ ID NO: 1 as well as sequences having about 60% or more, about 70% or more, about 80% or more, about 90% or more, about 95% or more, or about 99% or more (including any intervening ranges) sequence identity with SEQ ID NO: 1. In embodiments, cebR genes include nucleic acids having a sequence identity to SEQ ID NO: 1 of about 60% or more and having a sequence coverage to SEQ ID NO: 1 of about 70% or more, where sequence coverage indicates the percent of the total length of nucleic acids that are aligned.

The term "bglC gene" as used in the present disclosure indicates a nucleic acid sequence encoding a β-glucosidase enzyme in a *Streptomyces* or thaxtomin-producing *Actinomycete* species that is a modulator of thaxtomin production. In embodiments, "bglC genes" include the bglC gene of *S. scabies* (SEQ ID NO: 3) and variants and/or homologs (e.g., orthologs and paralogs) thereof retaining the function of modulating thaxtomin production. In embodiments "bglC genes" include nucleic acids having a sequence of SEQ ID NO: 3 as well as sequences having about 60% or more, about 70% or more, about 80% or more, about 90% or more, about 95% or more, or about 99% or more (including any intervening ranges) sequence identity with SEQ ID NO: 3. In embodiments, bglC genes include nucleic acids having a sequence identity to SEQ ID NO: 3 of about 60% or more and also having a sequence coverage of about 70% with SEQ ID NO: 3.

Discussion

In accordance with the purpose(s) of the present disclosure, as embodied and broadly described herein, embodiments of the present disclosure, in some aspects, relate to genetically modified *Streptomyces* bacteria capable of increased thaxtomin production, genetically modified *Streptomyces* bacteria with reduced activity of a CebR protein encoded by a cebR gene and/or reduced activity of a β-glucosidase enzyme encoded by the bglC gene, genetically modified *Streptomyces* bacteria including a mutation of a native cebR gene and/or a native bglC gene, methods of increasing thaxtomin production in *Streptomyces* bacteria, methods of suppressing CebR and/or BglC activity, methods of producing thaxtomin, and thaxtomin produced by the methods of the present disclosure.

Figure 1B:
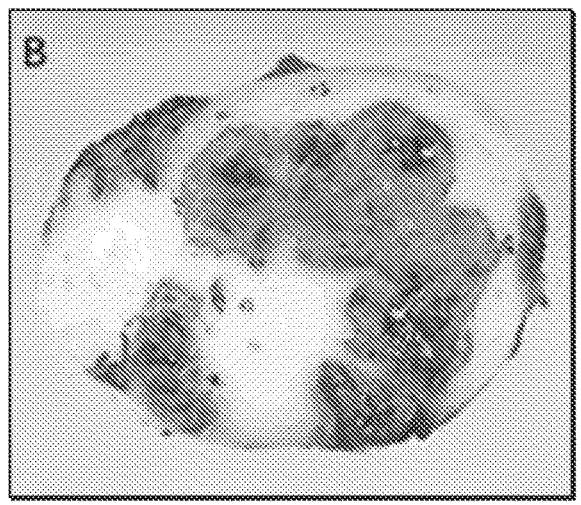
Figure 1C:
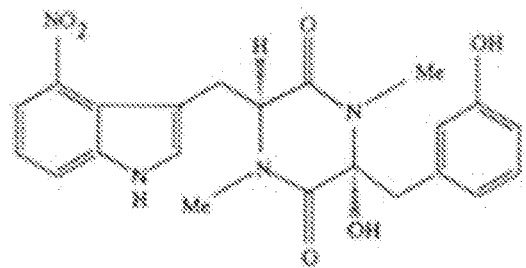

*Streptomyces* is a very large genus of Gram-positive, high G+C content bacteria that are mostly saprophytes and best known for the production of pharmaceutically- and agriculturally-important secondary metabolites (Hopwood 2007). Although several hundred species are known to date, only a handful are phytopathogenic (Loria et al. 2006). The best studied pathogens are *Streptomyces scabies, S. acidiscabies, S. turgidiscabies* and *S. ipomoeae*, which cause raised or pitted scab lesions on economically-important root and tuber crops like potato, radish, beet, peanut, and sweet potato (FIG. 1A, 1B). The primary virulence determinant of *S. scabies, S. acidiscabies* and *S. turgidiscabies* is the phytotoxin thaxtomin A (Loria et al. 2008) (FIG. 1C). It is member of a family of nitrated dipeptides formed by non-ribosomal peptide synthases out of the main components tryptophan, phenylalanine and nitric oxide derived from arginine (Loria et al. 2008; Barry et al. 2012).

Thaxtomin A (and other toxic thaxtomin compounds) primarily targets the cell wall in dividing and expanding plant cells through an alteration of expression of cell wall biosynthesis-related genes and depletion of cellulose synthase complexes from the plasma membrane. This causes extensive cell wall remodeling, characterized by reduced incorporation of crystalline cellulose into the plant cell wall, and is compensated by an increased amount of pectins and hemicelluloses (Scheible et al. 2003; Bischoff et al. 2009). Data have shown that thaxtomin provokes the same effects on plants, qualitatively as well as quantitatively, as the synthetic cellulose biosynthesis inhibitor isoxaben, making thaxtomin an excellent candidate as a natural herbicide (Heim et al. 1990; Bischoff et al. 2009). In 2001, King and Lawrence reported a study in collaboration with James A. Gray from Dow Agrosciences, Inc. to evaluate the potential of thaxtomin for use as a commercial herbicide. The biological properties of this novel phytotoxin raised an interest in using thaxtomin as a biological compound to control weeds (Marrone Bio Innovations 2009, 2010; Novozymes Biologicals 2011, 2012); however, thaxtomin production in wild type *Streptomyces* requires specialized cell culture media (such as media supplemented with cellobiose or other thaxtomin-inducing compounds), which can be expensive. Thus, the present disclosure provides genetically modified *Streptomyces* bacteria with the ability to produce thaxtomin compounds at an increase over wild type bacteria and in cell media in which wild type bacteria cannot produce thaxtomin, or produce it in only trace amounts, as well as methods for producing thaxtomin using such genetically modified bacteria.

Acquisition of genes required for virulence is only one step on the way to pathogenicity. Indeed, more subtle genetic changes are involved in adapting the expression of newly acquired genes to the environment and the life cycle of the recipient microorganism. For instance, a limited number of mutations in intergenic regulatory regions can transform a harmless strain into a pathogen. The distribution of cis-acting elements in the gene is an element involved in development of a strain-specific transcriptional response. These DNA motifs are targeted by transcription factors, which themselves are informed of the presence of environmental signals through direct interaction with membrane sensors or indirect association with elicitor transporters. The production of thaxtomin A itself is under transcriptional regulatory control including at least five global regulators belonging to the bid gene family involved in secondary metabolism and/or morphological differentiation of *Streptomyces* (Bignell et al. 2014) in addition to the thaxtomin biosynthesis pathway-specific transcriptional activator, TxtR. The multiplicity of global and specific regulators associated with thaxtomin production suggests that *S. scabies* may respond to multiple triggers that originate from plant material such as xylan-degradation products (Wach et al. 2007), suberin (Lauzier et al. 2008), and cellobiose, a product of cellulose degradation and the best-known elicitor of thaxtomin biosynthesis (Wach et al. 2007; Johnson et al. 2009) by directly targeting TxtR (Joshi et al. 2007).

Thus, as described in the examples below, proteins involved in regulation of thaxtomin regulation were identified, and genetically modified *Streptomyces* bacteria were produced with mutations affecting the activity of these proteins (e.g., by mutation in the genes encoding the proteins and/or by inhibition of the protein itself), resulting in modification of thaxtomin production. In exemplary embodiments, genetically modified *Streptomyces* bacteria have increased production of thaxtomin compounds, such as, but not limited to, thaxtomin A, and/or are capable of thaxtomin production in non-inducing conditions and on non-inducing media (e.g., conditions in which wild type *Streptomyces* do not produce thaxtomin or produce only trace amounts of thaxtomin).

As described in greater detail below, two genes were identified in *Streptomyces* species that produce proteins involved in the thaxtomin production pathway and whose disruption causes an increase in thaxtomin production in the modified bacterium and/or the ability to produce thaxtomin in non-inducing conditions. The genes include a cebR gene (e.g., SEQ ID NO: 1) and a bglC gene (e.g., SEQ ID NO: 3), which encode a CebR protein (e.g., SEQ ID NO: 2) and a β-glucosidase enzyme (e.g., SEQ ID NO: 4), respectively.

CebR is a repressor of thaxtomin biosynthesis in *Streptomyces* bacteria and responds directly to the presence of cellobiose (and possibly other inducing compounds), which binds and represses CebR thereby inducing thaxtomin production by the bacterium. CebR and variants and homologs of cebR are found in thaxtomin-producing *Streptomyces* bacterium. The sequence of cebR from *S. scabies* is illustrated in SEQ ID NO: 1. The present disclosure includes cebR sequences of SEQ ID NO: 1 as well as variants and homologs thereof defined above that encode a CebR protein that represses thaxtomin production, such as, but not limited to, cebR genes, variants, or homologs having about 60% sequence identity or more (with a sequence coverage of about 70% or more), with SEQ ID NO: 1.

The mechanism by which the bglC encoded enzyme acts to induce thaxtomin production is less clear, but like CebR, inactivation or reduced activity of the bglC β-glucosidase enzyme induces thaxtomin production. In embodiments, reduced activity of CebR and/or the bglC β-glucosidase enzyme increases thaxtomin production so that the affected bacterium constitutively produces thaxtomin, even in the absence of thaxtomin-inducing conditions. The sequence of an exemplary bglC gene (bglC from *S. scabies*) is illustrated in SEQ ID NO: 3. However, the scope of the present disclosure includes bglC genes having SEQ ID NO: 3 as well as variants and homologs thereof, as defined above, that encode a β-glucosidase enzyme, where disruption of the enzyme induces thaxtomin production, such as, but not limited to, bglC genes, variants, or homologs having about 60% or more sequence identity (with a sequence coverage about 70% or more) with SEQ ID NO: 3.

Although the methods of the present disclosure are generally described with respect to *Streptomyces* bacterium, since, to date, *Streptomyces* is the only species known to produce toxic thaxtomin compounds, to the extent that other species of Actinomycetes acquired thaxtomin biosynthetic genes via horizontal transfer or otherwise, the genetically modified bacteria and methods of the present disclosure are also applicable to such *Actinomycete* species with the acquired thaxtomin production capabilities and are included within *Streptomyces* in the scope of the present application. Thus for any of the genetically modified bacteria described herein and any methods of thaxtomin production described herein, it is understood that the scope of the present application also includes genetically modified Actinomycetes other than *Streptomyces* that also have or have acquired thaxtomin production capabilities.

The genetically modified bacteria of the present disclosure, methods of increasing thaxtomin compounds in *Streptomyces* bacteria, methods of producing thaxtomin, and thaxtomin produced by methods of the present disclosure are described in greater detail in the discussion below and following examples.

Genetically Modified Bacteria

Embodiments of the present disclosure include genetically modified *Streptomyces* bacteria including a mutation that reduces activity of a CebR protein encoded by a cebR gene, such that the genetically modified *Streptomyces* has increased production of a thaxtomin compound as compared to a corresponding wild type *Streptomyces* bacterium. Embodiments of the present disclosure also include genetically modified *Streptomyces* bacteria including a mutation that reduces activity of a β-glucosidase enzyme encoded by a bglC gene, such that the genetically modified *Streptomyces* has increased production of a thaxtomin compound as compared to a corresponding wild type *Streptomyces* bacterium. Embodiments also include genetically modified *Streptomyces* bacteria including a mutation that reduces activity of a CebR protein encoded by a cebR gene, a mutation that reduces activity of a β-glucosidase enzyme encoded by a bglC gene, or both mutations, such that the genetically modified *Streptomyces* has increased production of a thaxtomin compound as compared to a corresponding wild type *Streptomyces* bacterium.

In embodiments, the *Streptomyces* bacterium that is genetically modified is a *Streptomyces* species in which the corresponding wild type *Streptomyces* bacterium is capable of producing one or more thaxtomin compounds under standard thaxtomin-inducing conditions. In other words, the wild type *Streptomyces* bacterium can produce thaxtomin compounds in conditions as described above where *Streptomyces* species, such as *S. scabies* has been demonstrated to produce thaxtomin (e.g., Oat Bran Broth (OBB), Oat Bran Agar (OBA), and other cell culture mediums containing cellobiose or other thaxtomin inducer). The present disclosure also includes genetically modified bacteria from other actinomycetes that have acquired the ability to produce thaxtomin. In embodiments, the bacterium is selected from the group of *Streptomyces* species including, but not limited to, *Streptomyces scabies*, *S. acidiscabies*, and *S. turgidiscabies*. In specific embodiments the *Streptomyces* bacterium is a genetically modified *Streptomyces scabies* bacterium.

As discussed above, some wild type *Streptomyces* species (e.g., *Streptomyces* scabies, *S. acidiscabies*, and *S. turgidiscabies*, etc.) produce thaxtomin compounds under certain conditions, defined herein as thaxtomin-inducing conditions, but cannot produce thaxtomin constitutively or in all conditions, or in the absence of certain triggers/inducers (for example, but not limited to, cellobiose). In embodiments, the genetically modified *Streptomyces* bacteria of the present disclosure produce one or more thaxtomin compounds in the absence of at least one carbohydrate that reduces CebR DNA-binding activity (such as, but not limited to, cellobiose, cellotriose, and cellohexaose). In embodiments, the carbohydrate is selected from cellobiose, cellotriose, and cellohexaose. In an embodiment, the carbohydrate is cellobiose. The genetically modified *Streptomyces* bacteria of the present disclosure may produce one or more thaxtomin compounds, such as, but not limited to: thaxtomin A, thaxtomin, B, thaxtomin C, thaxtomin D, and the like. In embodiments, the genetically modified *Streptomyces* bacteria of the present disclosure may produce at least thaxtomin A, which is believed to be the most physiologically active and may be a precursor to other thaxtomin compounds.

The genetically modified *Streptomyces* bacteria of the present disclosure can be genetically modified in various ways in order to reduce the activity of a CebR protein or β-glucosidase enzyme encoded by a cebR gene or a bglC gene, respectively, such that the genetically modified *Streptomyces* has increased production of a thaxtomin compound as compared to a corresponding wild type *Streptomyces* bacterium. In general, any genetic modification of the bacterium that results in reduced activity of the target proteins (CebR and β-glucosidase) are intended to be included in the scope of the present disclosure. In embodiments, the genetic modification can include a mutation of the native genetic material of the bacterium (e.g., a mutation such as, but not limited to, an insertion, deletion, or rearrangement of the native (e.g., wild type) genetic material of the bacterium). In other embodiments, the genetic modification can include a mutation resulting from introduction of exogenous genetic material (e.g., nucleic acid sequence) into the bacterium (e.g., via transfection).

Thus, in embodiments, the genetically modified bacterium includes a mutation of a native cebR and/or bglC gene, where the mutation reduces production or functionality of a protein encoded by the gene. In embodiments, the mutation of the native cebR and/or bglC gene may inhibit expression of the gene or the functionality of a resulting gene product. For example, the mutation may inhibit transcription of the cebR and/or bglC gene into mRNA, may inhibit translation of the mRNA into the CebR protein and/or β-glucosidase enzyme, may completely remove the cebR and/or bglC gene (which also inhibits transcription), may include a mutation of the cebR and/or bglC gene that still allows transcription but results in a non-functional CebR protein, and the like.

In embodiments, the mutation of cebR and/or bglC (e.g., the "target" gene) is a null mutation (e.g., the target gene is removed from the genome or transcription of the gene is otherwise virtually completely suppressed). In embodiments, the null mutation is obtained by replacing the target gene with a deletion cassette. In embodiments, the replacement gene in the deletion cassette can be any gene other than the gene being replaced. In embodiments, the replacement gene provides a detectable signal (such as, but not limited to, antibiotic resistance, fluorescence, color change, etc.) to allow for detection of mutant cells (e.g., cells containing the replacement gene in place of the target gene). In embodiments, the deletion cassette is included in a vector, plasmid, or other system useful for effecting transformation and genetic recombination. In embodiments, primers are used that have sequences including regions homologous to flanking regions of the target gene as well as of the replacement gene in the deletion cassette in order to facilitate the replacement of the target gene with the replacement gene. In embodiments of the present disclosure, the deletion cassette includes an apramycin resistance gene having a nucleotide sequence of SEQ ID NO: 42. In some embodiments where the target gene is a cebR gene having a nucleotide sequence of SEQ ID NO: 1 a deletion cassette including SEQ ID NO: 42 and forward and reverse primers having sequence ID NOS: 8 and 9 can be used to genetically modify *Streptomyces* bacteria of the present disclosure to produce cebR null mutants. In some embodiments where the target gene is a bglC gene having a nucleotide sequence of SEQ ID NO: 3, a deletion cassette including SEQ ID NO: 42 and forward and reverse primers having sequence ID NOS: 28 and 29 can be used to genetically modify *Streptomyces* bacteria of the present disclosure to produce cebR null mutants.

In embodiments of the present disclosure, the genetically modified bacterium has reduced activity of CebR and/or β-glucosidase because it does not produce functional CebR and/or β-glucosidase, encoded by cebR or bglC, respectively, either due to lack of production (e.g., lack of transcription and/or translation) or due to production of a non-functional protein.

While some genetic mutations, discussed above, reduce activity of CebR and/or β-glucosidase and thereby increase thaxtomin production by including a mutation of the encoding gene itself (e.g., cebR and/or bglC), other mutations of the genetically modified bacteria of the present disclosure may include an exogenous nucleic acid sequence that reduces the activity of the target proteins, such as by suppressing expression and/or by interacting with the protein itself to inhibit activity. In embodiments, the mutation of the genetically modified *Streptomyces* bacterium of the present disclosure includes an exogenous nucleic acid sequence introduced into the bacterium, wherein the exogenous nucleic acid sequence reduces activity of a CebR protein encoded by the cebR gene. In embodiments, the exogenous nucleic acid sequence may include one or more RNAi sequences (e.g., an miRNA sequence and/or siRNA sequence) that inhibit expression of cebR and/or bglC, thereby resulting in increased thaxtomin production by the genetically modified bacterium.

Other methods known to those of skill in the art for reducing the activity of a target protein can be used within the scope of the present disclosure to provide genetically modified *Streptomyces* bacteria having a mutation that reduces the activity of a CebR protein encoded by a cebR gene and or a or β-glucosidase encoded by a bglC gene, such that the genetically modified *Streptomyces* has increased production of a thaxtomin compound as compared to a corresponding wild type *Streptomyces* bacterium.

Methods of Increasing Production of a Thaxtomin Compound in *Streptomyces*

The present disclosure also provides methods of increasing production of thaxtomin compound in a *Streptomyces* bacterium (or other *Actinomycete* that has acquired the ability to product thaxtomin). In general, methods of the present disclosure for increasing thaxtomin production in a *Streptomyces* bacterium include suppressing the activity of a CebR protein encoded by a cebR gene, suppressing the activity of a β-glucosidase enzyme encoded by a bglC gene, or both. In embodiments, the method includes providing a *Streptomyces* bacterium from a species capable of producing one or more thaxtomin compounds under standard thaxtomin-inducing conditions and genetically modifying the *Streptomyces* bacterium by creating a mutation in the bacterium that results in reduced activity of a CebR protein encoded by a cebR gene and/or of a β-glucosidase enzyme encoded by a bglC gene, such that the genetically modified *Streptomyces* has increased production of a thaxtomin compound as compared to a corresponding wild type *Streptomyces* bacterium. As discussed above, genetically modifying the bacterium can be achieved by any of the approaches discussed above. For example, the method may include genetically modifying the bacterium by creating a mutation in the genome (e.g., native genetic material) of the bacterium and/or creating a mutation by introducing an exogenous nucleic acid sequence into the bacterium (e.g., via an expression vector or other expression system).

As described above, in embodiments the mutation may be a mutation of a native cebR and/or bglC gene that reduces the production or functionality of a CebR protein or β-glucosidase enzyme encoded by the respective mutated gene. Suppressing the activity of the CebR protein and/or the β-glucosidase enzyme, in embodiments, can include genetically modifying the *Streptomyces* bacterium to inhibit expression of the cebR gene and/or bglC gene encoding the CebR protein and/or β-glucosidase enzyme, respectively. In embodiments, the mutation can be a null mutation of the cebR and/or bglC gene, such as by inserting a deletion cassette into the genome to remove/replace the cebR and/or bglC gene, thereby inhibiting production of CebR protein or β-glucosidase enzyme encoded by the removed/replaced gene. In embodiments, the deletion cassette can be as described above.

In embodiments of methods of increasing thaxtomin production in *Streptomyces* bacteria, the bacteria are modified by creating a mutation in the bacterium by introducing an exogenous nucleic acid sequence into the bacterium, where the exogenous nucleic acid sequence, or its expression product, reduces activity of the target protein (e.g., cebR encoded by cebR and/or β-glucosidase enzyme encoded by bglC). In embodiments, as discussed above, the exogenous nucleic acid sequence includes an RNAi sequence that suppresses production (e.g., by suppressing translation of mRNA sequences encoding the target protein) or function/activity of the target CebR or β-glucosidase enzyme.

Other methods known to those of skill in the art can be used to introduce a mutation into the *Streptomyces* bacteria that results in decreased activity of cebR and/or β-glucosidase and consequently increased thaxtomin production. Such methods are intended to be included in the scope of the present application.

Methods of Producing Thaxtomin

The present disclosure also includes methods of producing thaxtomin. Embodiments of such methods include culturing genetically modified *Streptomyces* bacteria, where the genetically modified *Streptomyces* bacteria comprise a mutation of a native cebR gene, a mutation of a native bglC gene, or both (such as described above), where the mutation reduces production or functionality of a CebR repressor encoded by the cebR gene, a β-glucosidase enzyme encoded by the bglC gene, or both, so that the modified *Streptomyces* bacteria produce thaxtomin. In the methods of producing thaxtomin of the present disclosure, the genetically modified *Streptomyces* bacteria exhibit increased production of thaxtomin compound as compared to a corresponding wild type *Streptomyces* bacteria. As described above, embodiments of the genetically modified *Streptomyces* bacteria of the present invention constitutively produce thaxtomin in environmental conditions (e.g., standard growth medium) where wild type *Streptomyces* bacteria would not be able to produce thaxtomin or may only produce trace amounts. In embodiments of the methods of the present disclosure for producing thaxtomin, the thaxtomin produced by the genetically modified *Streptomyces* bacteria is collected and/or extracted from the cell culture. After collection/extraction of the thaxtomin from the cell culture, the thaxtomin may be further extracted/separated from the culture media, and/or the extracted thaxtomin may then be subject to further isolation and/or purification steps as needed or desired.

The isolated and/or purified thaxtomin compound isolated from the genetically modified *Streptomyces* bacteria of the present disclosure can then be used for various purposes, such as in the production of certain herbicides. Thus, the methods of the present disclosure also include methods of making herbicides including thaxtomin by producing thaxtomin according to the methods of the present disclosure and using the thaxtomin to produce the herbicide. The present disclosure also includes thaxtomin compounds produced by the methods of making thaxtomin of the present disclosure described above.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The present example describes the identification of CebR, the cellulose/cellooligossaccharide and cellobiose utilization regulator, as master repressor of thaxtomin biosynthesis in thaxtomin-producing *Streptomyces* species. The example describes a modified *Streptomyces* strain capable of constitutive production of thaxtomin compounds regardless of the presence of cellobiose or other cellulose degradation products capable of inducing thaxtomin production. The results demonstrate how and why (the molecular mechanism) the inactivation of cebR results in the constitutive production of thaxtomin independently of cellobiose supply in the culture medium. The presence of CebR-binding sites associated with thaxtomin biosynthetic genes in other thaxtomin-producing streptomycetes (except *Streptomyces ipomoeae*), or other thaxtomin-producing actinomycetes, allow application of these methods beyond the species *S. scabies* 87-22.

Results & Discussion

Figure 2:
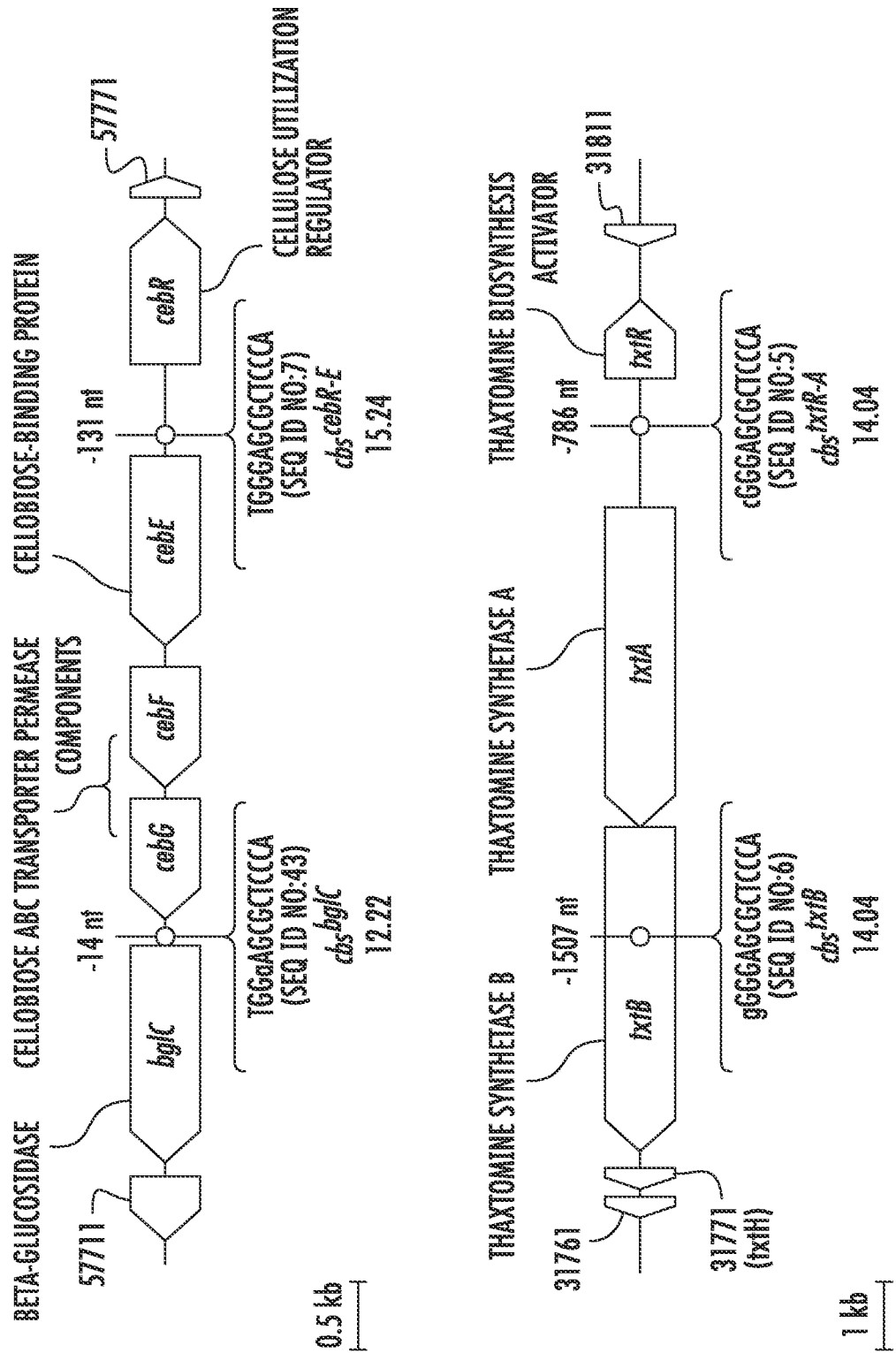
FIG. 2 shows the CebR-binding sites associated with the cellobiose uptake system and the thaxtomin biosynthetic genes. Numbers below cbs are scores obtained by the predicted CebR target sequences using the PREDetctor software and the position weight matrix. Numbers associated with genes/orfs are SCAB numbers from the annotated genome of *S. scabies* (strain 87-22).

Identification of CebR DNA-Binding Sites Associated with the Thaxtomin Biosynthetic Genes The identification of transcription factors involved in the control of thaxtomin was performed by scrutinizing the genome of *Streptomyces scabies* for the occurrence of putative cis-acting elements of well-characterized DNA-binding proteins. Position weight matrices were generated from the compilation of DNA motifs bound by a series of regulators that were selected due to their notorious direct or indirect implication in secondary metabolite biosynthesis and/or morphological differentiation in streptomycetes. The PREDetector software (Hiard et al. 2007) identified two 14-bp palindromic sequences similar to CebR boxes (henceforth cbs for CebR-binding sites) and physically associated with the thaxtomin biosynthetic genes, txtA and txtB, and the pathway-specific regulatory gene, txtR (FIG. 2). The bioinformatic method used to identify DNA motifs in the chromosome of *S. scabies* is described in the material and methods section.

The cGGGAGCGCTCCCA sequence ($cbs^{txtR-A}$) (SEQ ID NO: 5) lies in the intergenic region between txtR and txtA at positions −786 nt and −900 nt upstream of txtR and txtA, respectively, whereas the gGGGAGCGCTCCCA sequence ($cbs^{txtB}$) (SEQ ID NO: 6) lies at position +1507 nt within the coding sequence of txtB (FIG. 2). Both sequences display only one single mismatch with the reported 14-bp cbs palindromic consensus sequence TGGGAGCGCTCCCA ($cbs^{cebR-E}$) (SEQ ID NO: 7) (Marushima et al. 2009). FIG. 2 also illustrates that a 14-bp sequence, TGGAAGCGCTCCA ($cbs^{bglC}$) (SEQ ID NO: 43), lies −14 nt upstream of bglC with only a single bp mismatch with $cbs^{cebR-E}$ (SEQ ID NO: 7).

CebR has been identified as the repressor of cellulose/cellooligosaccharides/cellobiose utilization in streptomycetes (Schlösser et al. 2000; Marushima et al. 2009) and, in addition, it has also been shown to trigger morphogenesis in *Streptomyces griseus* (Marushima et al. 2009). In *S. griseus*, binding of cellobiose to CebR relieves its grip on the specific cbs and allows for transcription of the downstream genes. Interestingly, cellobiose is also known as the best elicitor of thaxtomin production in *S. scabies, S. acidiscabies* and *S. turgidiscabies* (Joshi et al. 2007; Wach et al. 2007).

Inspection of the full length chromosome of *S. scabies* further revealed the presence of palindromic cbs within the intergenic region between cebR (scab57761) itself and cebE (scab57751, $cbs^{cebE-R}$) encoding the orthologue of the streptomycete cellobiose-binding component of an ABC-type transporter (FIG. 2), as well as upstream of bglC (scab57721, $cbs^{bglC}$) encoding the orthologue of the β-glucosidase associated with the cellobiose/cellotriose-specific ABC transporter in streptomycetes and which cleaves the β1→4 glycosidic bond linking the two glucose molecules.

Figure 3:
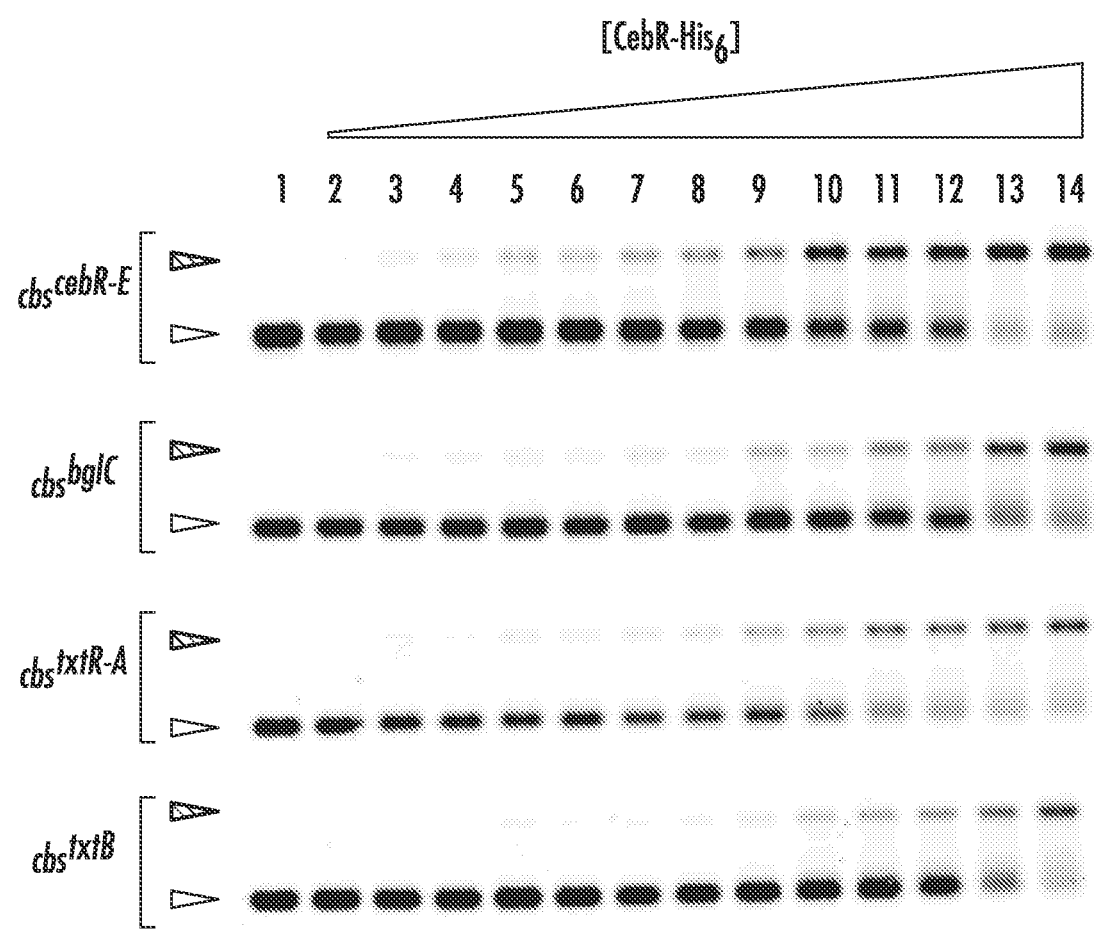
FIG. 3 shows an electromobility gel shift assay (EMSA) demonstrating CebR binding to DNA motifs identified within the txtRA and cebRE intergenic region, upstream of bglC and within txtB. Numbers 1 to 14 refer to increasing concentrations of pure CebR-His6, i.e., 0 (free probe, 30 nM), 80, 160, 240, 320, 400, 480, 560, 640, 720, 960, 1200, 1600, 3200 nM, respectively.

Electromobility gel shift assays (EMSAs) were performed in order to assess binding of the *S. scabies* CebR regulator ($CebR^{sca}$) to the in silico predicted cbs. The scab57761 gene was cloned into pET-22b and overexpressed in *Escherichia coli* Rosetta (DE3) cells. The resulting recombinant His-tagged CebR (CebR-His6) was purified from the IPTG-induced *E. coli* cytoplasmic extracts by Nickel-NTA affinity column. EMSAs performed with 34-bp double stranded, Cy5-labelled probes (SEQ ID NOs: 18 & 19 ($cbs^{txtR-A}$), SEQ ID NOs: 20 & 21 ($cbs^{cebE-R}$), SEQ ID NOs: 22 & 23 ($cbs^{txtB}$), and SEQ ID NOs: 24 & 25 ($cbs^{bglC}$)) centered on the putative cbs showed that $cbs^{txtR-A}$ and $cbs^{txtB}$ were strongly bound by $CebR^{sca}$, even with a 20-fold excess of non-specific DNA (FIG. 3). Under the same conditions, strong CebR-binding to cbs$^{cebE-R}$ and cbs$^{bglC}$, which were used as positive controls of genes known to be directly controlled by CebR (Schlösser 2000; Marushima 2009), was observed (FIG. 3). EMSAs performed with CebR pre-incubated with cellobiose and cellooligosaccharides revealed that cellobiose was the best allosteric effector, inhibiting CebR from binding to its DNA targets (FIG. 4).

Figure 4:
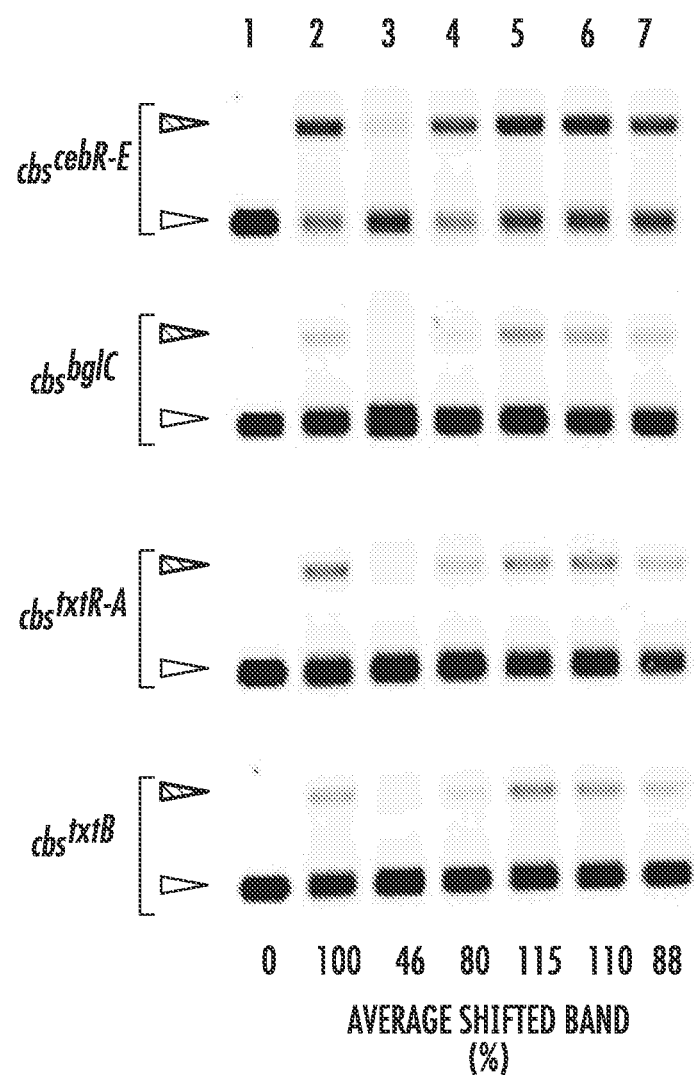
FIG. 4 shows EMSAs demonstrating cellobiose as the best allosteric effector of CebR. Numbers 1 and 2 refer to EMSAs with free probes (6 nM) and with probes incubated with CebR-His$_6$, respectively. Numbers 3 to 7 refer to EMSAs with CebR-His$_6$ pre-incubated with oligosaccharides, i.e. cellobiose (3), cellotriose (4), cellotetraose (5), cellopentaose (6), and cellohexaose (7). Note that cellobiose (3) is the best oligosaccharide for preventing CebR interaction with all CebR-binding sites.
Figure 5:
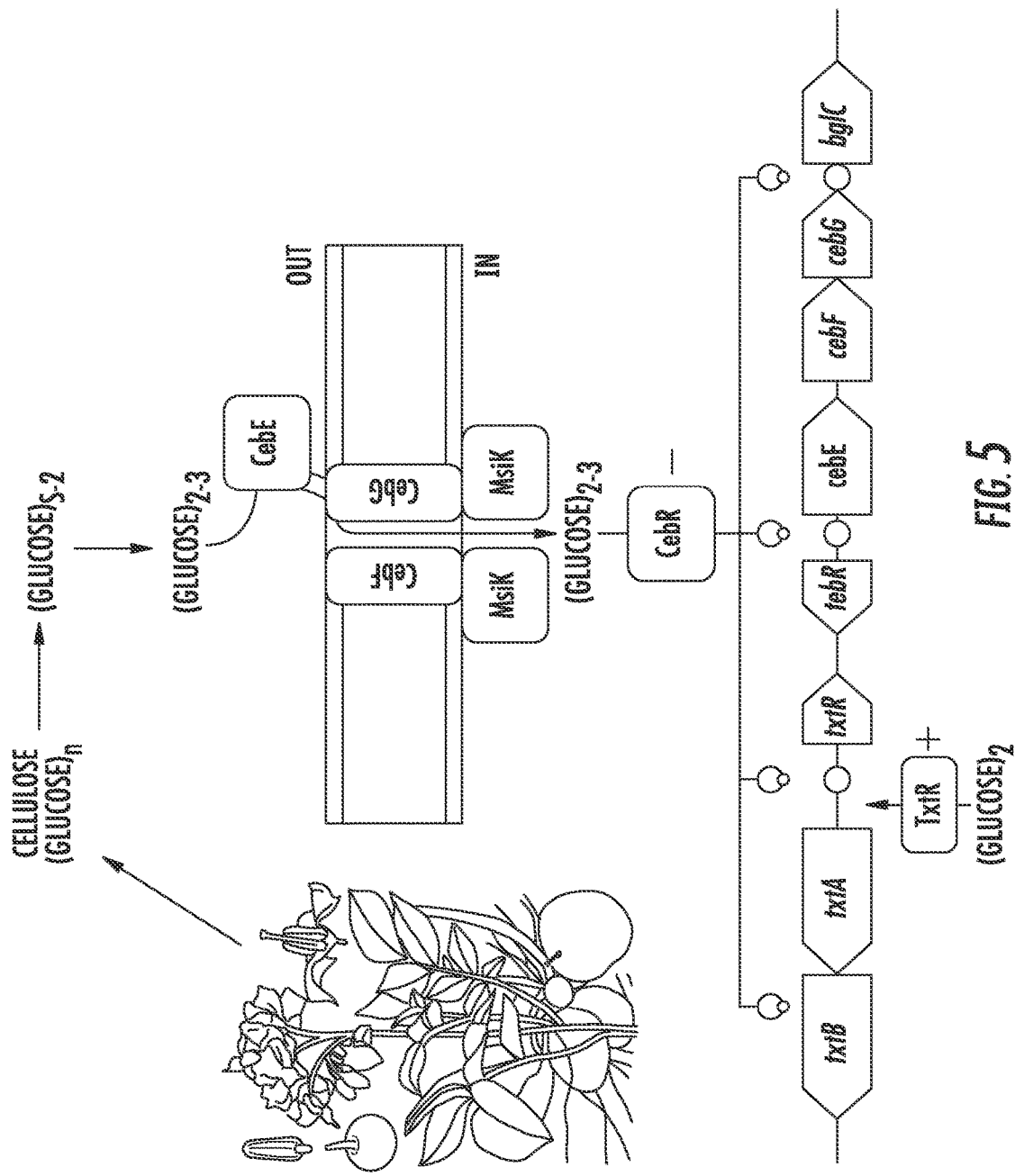
FIG. 5 illustrates a model of cellobiose-dependent production of thaxtomin in *S. scabies*.

Quantification of the shifted bands presented in FIG. 4 revealed that cellobiose (lane 3), cellotriose (lane 4), and cellohexaose (lane 7) were able to impair the CebR DNA-binding ability by 56%, 20%, and 12%, respectively. Experimental in vitro validations of predicted cis-acting elements allowed proposing a signaling pathway from cellobiose sensing and transport to thaxtomin biosynthesis (FIG. 5). The putative working model suggests that cellobiose is transported via the ABC-type transporter CebEFG and that the energy for this active transport is most-likely provided by ATP hydrolysis through the multiple sugar importer MsiK (Schlösser et al. 1997). Once inside the cell, cellobiose (and to a lesser extent cellotriose) prevents CebR-binding to cbs$^{txtR-A}$ and cbs$^{txtB}$ allowing expression of txtA, txtB and txtR. Consequently, TxtR complexed to cellobiose would be able to increase the expression levels of txtA and txtB, the thaxtomin biosynthetic genes.

Deletion of cebR Results in Constitutive Production of Thaxtomin

Figure 6:
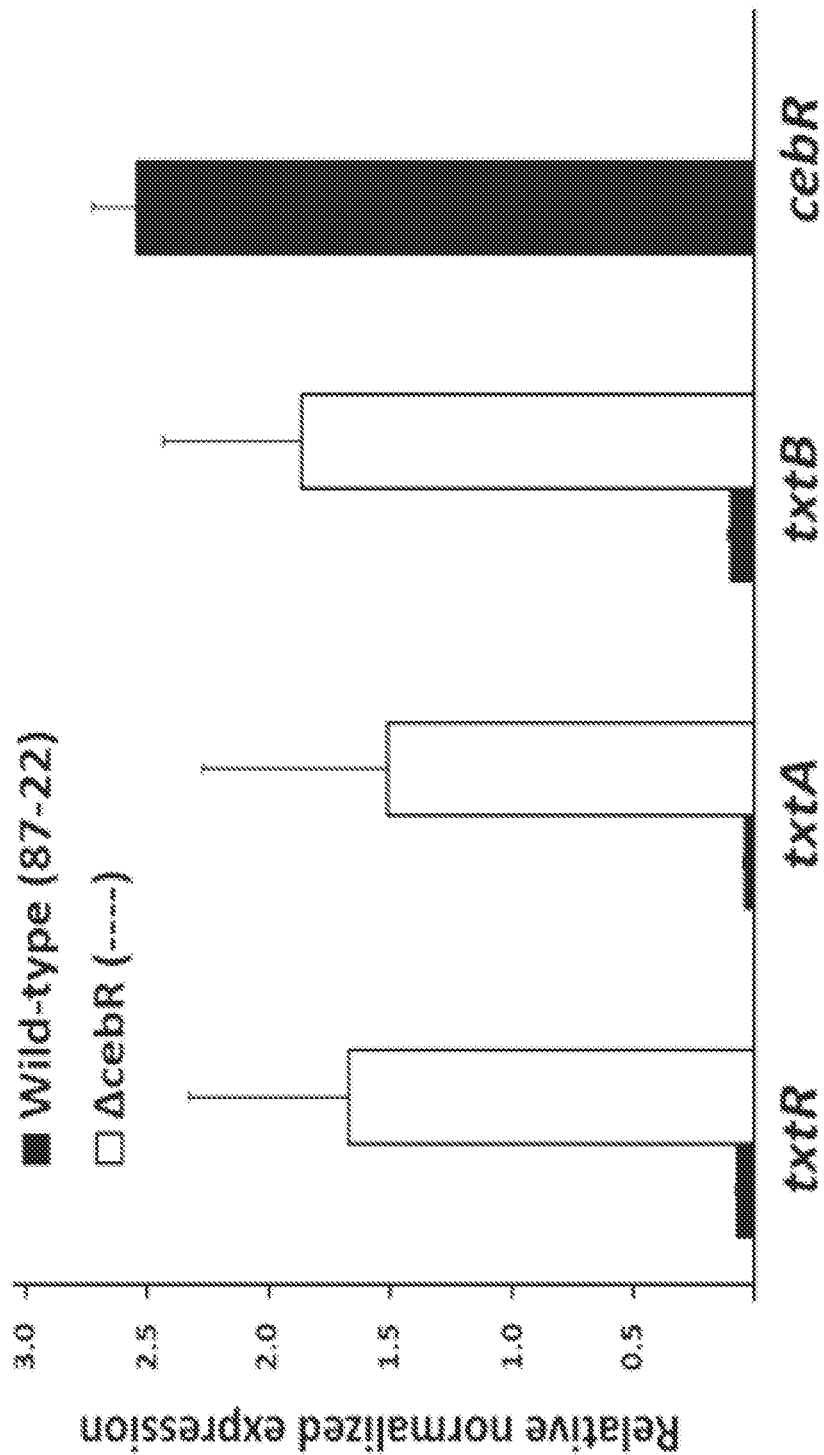
FIG. 6 shows the effect of cebR deletion in *S. scabies* on the transcription levels of the thaxtomin biosynthetic and regulatory genes. Quantitative real-time RT-PCR analysis of gene expression levels in *S. scabies* 87-22 and in the ΔcebR strain. Data were normalized using the gyrA, murX and the hrdB gene as internal controls. Mean normalized expression levels (±standard deviation) from three biological replicates analyzed in triplicate are shown.

The signaling cascade presented in FIG. 5 suggests a role for CebR in the production of thaxtomin in plant pathogenic streptomycetes. In order to evaluate the role of this regulator in controlling the expression levels of the thaxtomin biosynthetic genes txtA and txtB, cebR null mutants were generated in S. scabies (ΔcebR), and its thaxtomin production was assessed on various media. Quantitative real-time PCR (qRT-PCR) on RNA extracted from S. scabies wild-type (strain 87-22) and its cebR null mutant showed that the inactivation of cebR resulted in overexpression of txtA, txtB and txtR, respectively (FIG. 6). This result confirms that, despite the unusual position of cbs$^{txtR-A}$ and cbs$^{txtB}$, further upstream of the target txtA and txtR genes and within the coding region of txtB (FIG. 2), respectively, the identified DNA motives are truly functional cis-acting elements.

Moreover, the search for similar sequences in other thaxtomin-producing Streptomyces pathogens confirmed the occurrence of cbs in their thaxtomin biosynthetic regions. In S. acidiscabies, the oldest pathogenic species that displays a similar response to cellobiose, three cbs signatures were identified within the thaxtomin biosynthetic cluster i.e. one upstream of txtA (−787 nt), one within txtA (+32 nt) and one within txtB (+1559 nt). In S. turgidiscabies one cbs was found within txtA (+32 nt) and one within txtB (+1508 nt). A third cbs was found at position −1444 nt upstream of txtR. No cbs associated with thaxtomin production could be identified in S. ipomoeae which, in contrast to the previously mentioned pathogenic species, appears to produce only thaxtomin C and is not responsive to cellobiose or other oligosaccharides in terms of toxin production (Guan et al. 2012). Therefore, the occurrence of cbs upstream of or within the txt genes correlates with the observed cellobiose-dependent production of thaxtomin A in pathogenic Streptomyces species.

Figures 7A, 7B:
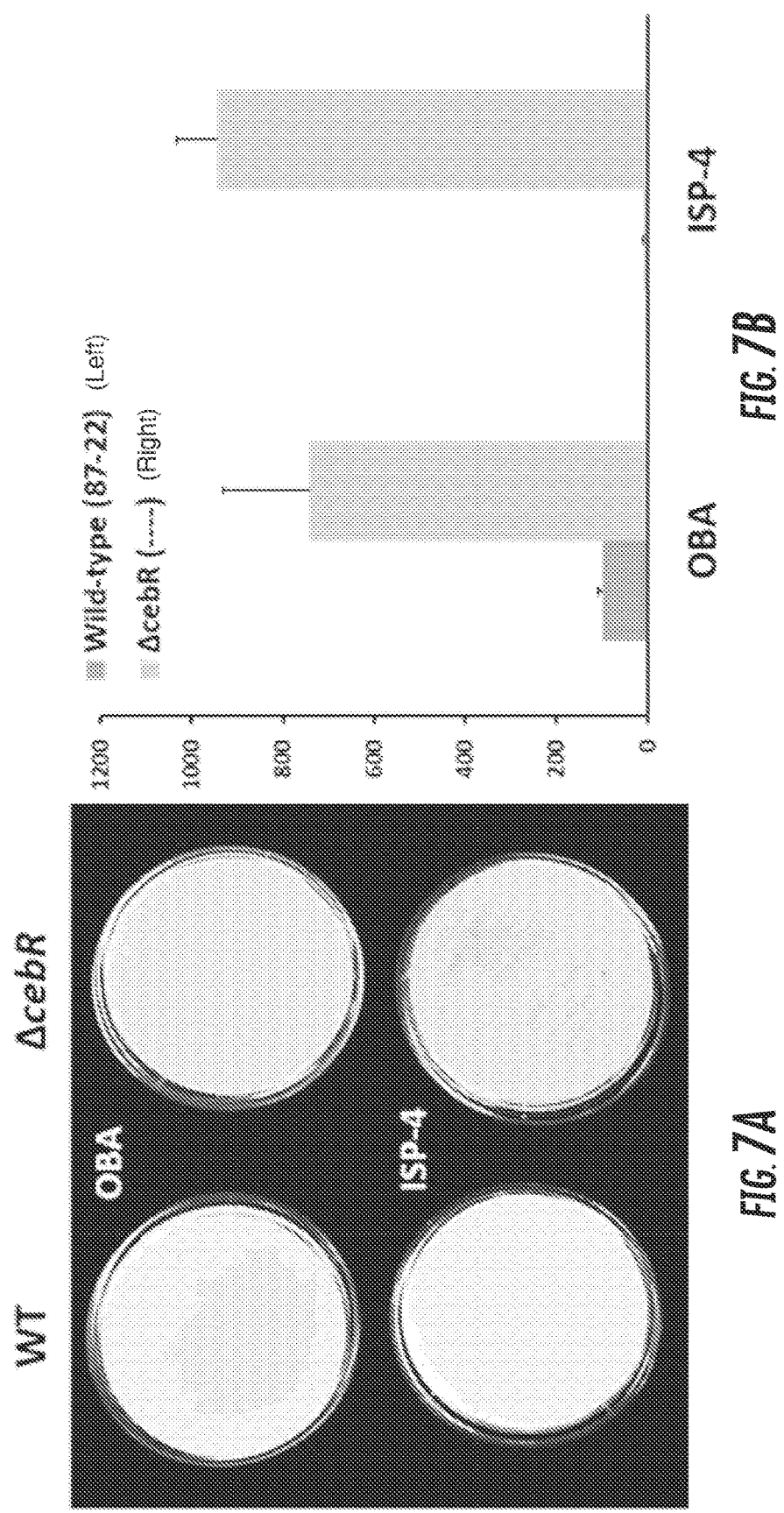
FIGS. 7A-7B show effects of the cebR deletion on thaxtomin production in *S. scabies*.
Figures 9A, 9B:
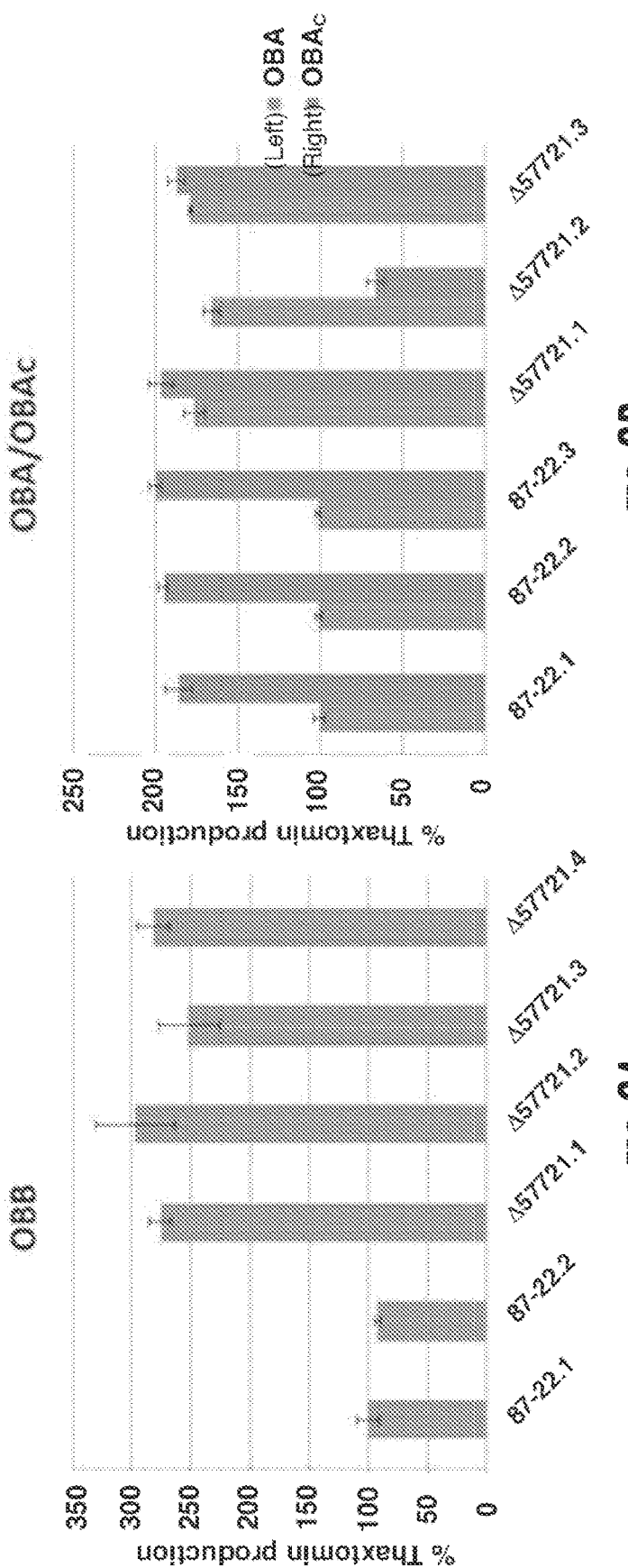
FIGS. 9A-9B show production of thaxtomin A by wild type *S. scabies* (87-22) and by the *S. scabies*β-glucosidase mutant (Δ57721) in OBB (FIG. 9A) and on OBA plates and OBA and OBA with cellobiose (FIG. 9B).
Figure 10:
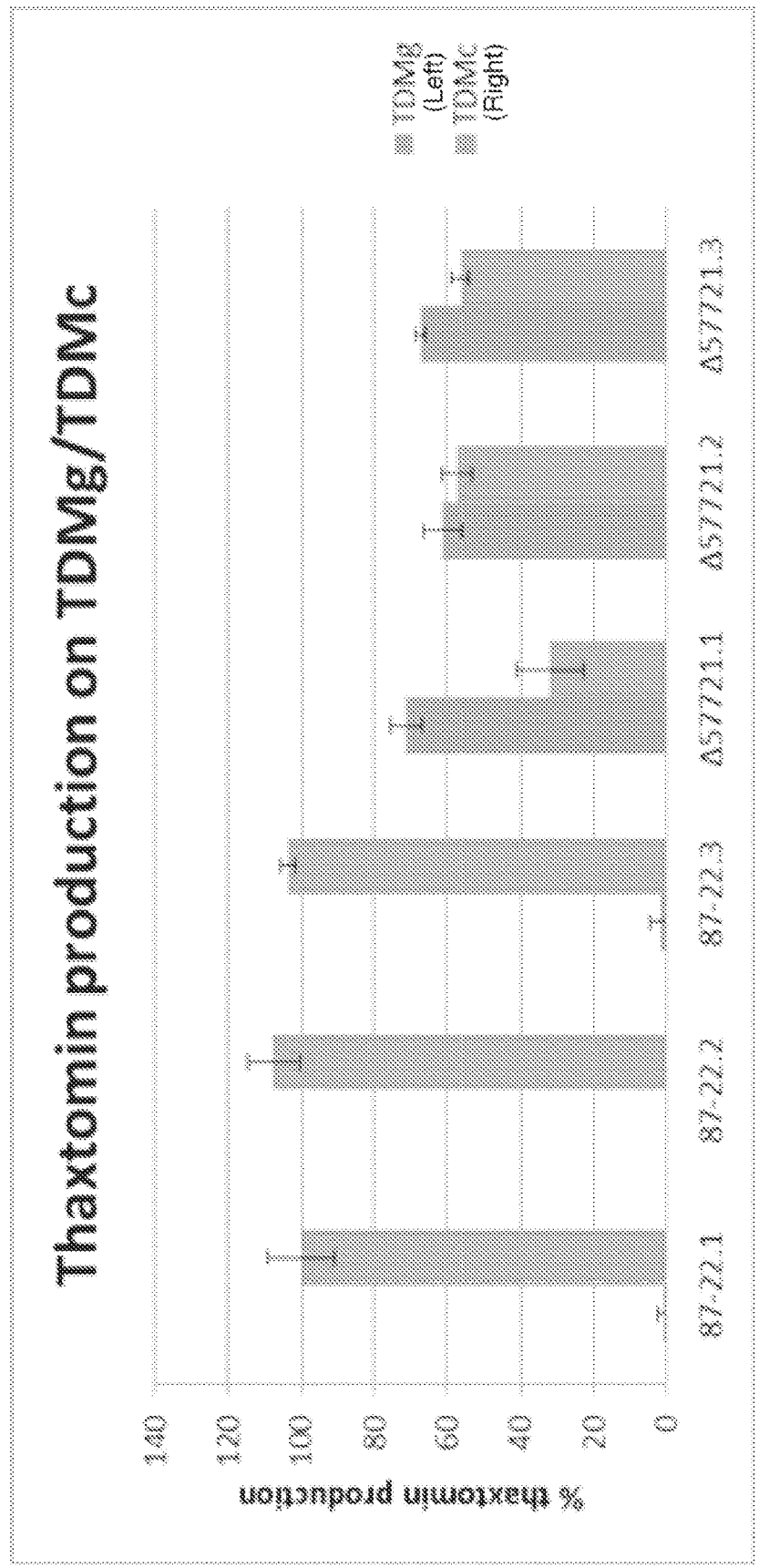
FIG. 10 shows production of thaxtomin A by wild type *S. scabies* (87-22) and by the *S. scabies*β-glucosidase mutant (Δ57721) on TDM agar plates with glucose and cellobiose, respectively, as the only carbon source.
Figure 11:
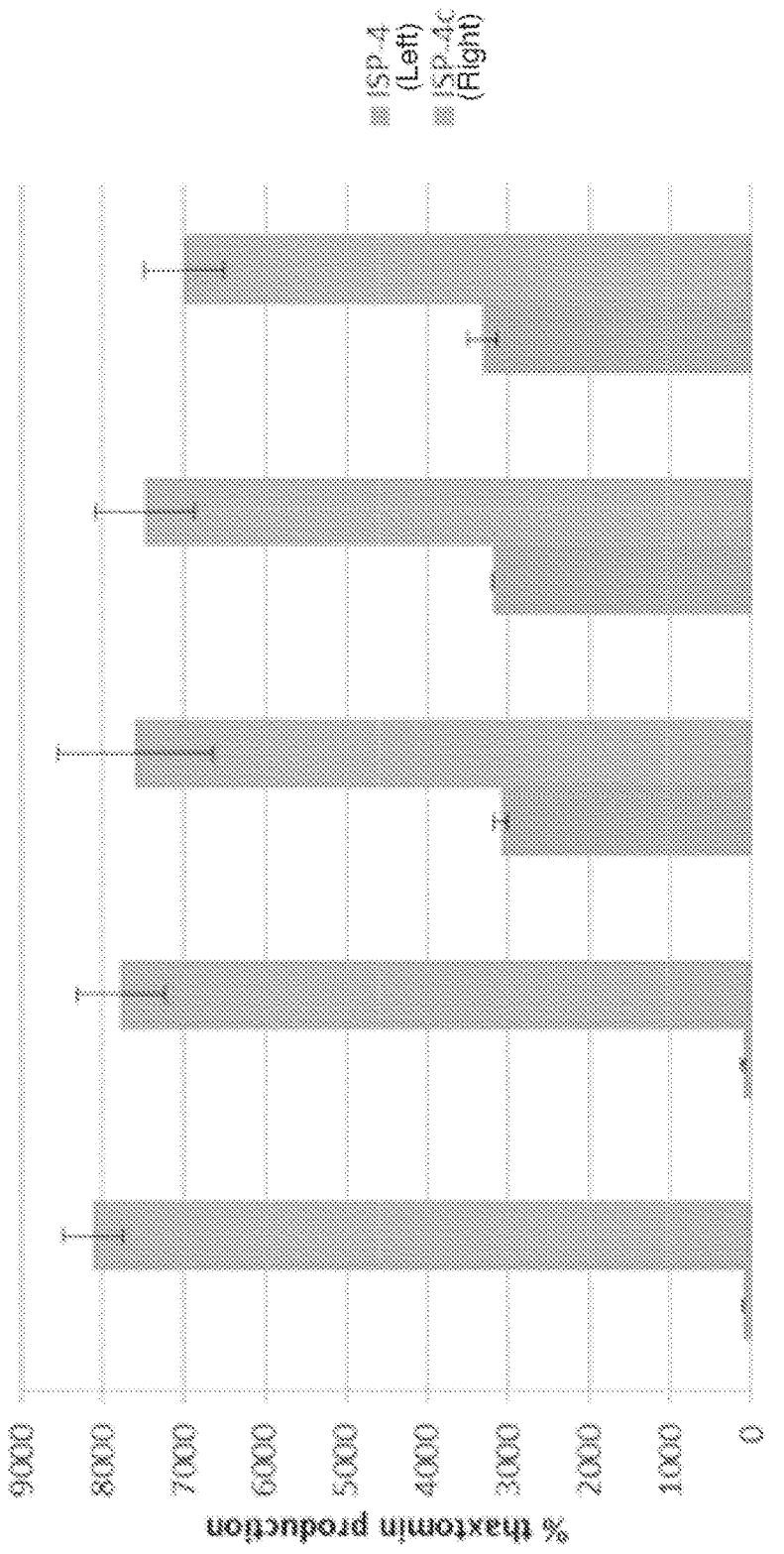
FIG. 11 is a bar graph illustrating production of thaxtomin A by wild type *S. scabies* (87-22) and by the *S. scabies*β-glucosidase mutant (Δ57721) on ISP-4 plates and ISP-4 with cellobiose.

Thaxtomin production levels of both the S. scabies and the cebR null mutant were also assessed on Oat Bran Agar (OBA), an undefined complex medium known to induce thaxtomin production (Johnson et al. 2007, incorporated herein by reference), and ISP-4. On OBA the cebR mutant overproduced thaxtomin, which is bright yellow in color, compared to the wild-type (FIG. 7A). When streaked out on plates containing the International Streptomyces Project (ISP) mediumISP-4, the S. scabies strain where the gene coding for the CebR repressor had been deleted (ΔcebR) produced thaxtomin without the addition of the cellobiose inducer (FIG. 7A). The same results were observed with liquid cultures (Oat Bran Broth, OBB).

Since ISP-4 medium (containing soluble starch as carbon source) is not known to induce toxin production (other than occasional trace amounts that could result from contamination) in S. scabies, this result demonstrates that the mutant of S. scabies was able to produce thaxtomin A independent of the presence the elicitor cellobiose. Extraction of thaxtomin from the plates and analysis by HPLC confirmed the overproduction of the toxin by the cebR mutant on ISP-4 (FIG. 7B). ΔcebR complemented with the S. scabies cebR gene and its upstream region restores the cellobiose-dependent induction of thaxtomin, demonstrating that the phenotype of the mutant is caused by the chromosomal deletion of orf scab57761 (FIGS. 8A-B).

The production of thaxtomin by both strains grown on ISP-4 with and without cellobiose supply was compared. As shown in FIGS. 8A and 8B, addition of cellobiose triggers a significant increase of thaxtomin production in a wild-type or ΔcebR background, respectively. The further increase in toxin production by the mutant upon addition of cellobiose is most likely due to the function of cellobiose as ligand of the transcriptional activator TxtR, which drives the expression of the thaxtomin biosynthetic genes txtA and txtB (Joshi et al. 2007) (FIG. 5).

Conclusion

The present data suggest that the methods of the present disclosure for increasing thaxtomin production through the deletion of cebR is, in addition to S. scabies, is applicable to S. turgidiscabies and S. acidiscabies, as well as in any other streptomycete or actinomycete that would possess a cbs associated with thaxtomin biosynthetic or regulatory genes.

Material and Methods

Bacterial Strains, Media, Chemicals, and Culture Conditions

All strains and plasmids used in this study are described in Table 1. Escherichia coli strains were cultured in Luria-Bertani (LB) medium at 37° C. Streptomyces strains were routinely grown on International Streptomyces Project medium 4 (ISP-4; BD Biosciences), Soy Flour Mannitol agar (SFM; Kieser et al. 2000), or in Tryptic Soy Broth (TSB; BD Biosciences) at 28° C. Where required, the medium was supplemented with antibiotics at the following concentrations: apramycin (Apr, 100 µg/ml), kanamycin (Kan, 50 µg/ml), chloramphenicol (Cml, 25 µg/ml), thiostrepton (Thio, 25 µg/ml), and/or nalidixic acid (NA, 50 µg/ml). Spore suspensions were prepared from 7- to 10-day-old ISP-4 plates and maintained as 20% glycerol stocks at −80° C. Cellobiose, cellotriose, cellotetraose, cellopentose, and cellohexaose were purchased at Megazyme (Ireland).

CebR Regulon Prediction in Streptomycetes

Creation of the position weight matrix (PWM) and the computational prediction of the CebR regulon in S. scabies were performed with the PREDetector software (Hiard et al. 2007) as described previously (Craig et al. 2012, incorporated herein by reference for PWM and computational prediction). DNA motifs known to be bound by CebR in S. griseus (Marushima et al. 2009) were used as a training set to generate the PWM (PWM-CebR$^{gri}$). This PWM-CebR$^{gri}$ was used to scan the genome of *Streptomyces* species for similar DNA motifs using a cut-off score of 8 (with a reliability threshold of 10).

Generation of the cebR and bglC Gene Deletions in *S. scabies* 87-22

Deletion mutants in *S. scabies* 87-22 were created using the REDIRECT PCR targeting methodology (Gust et al. 2003, incorporated herein by reference) replacing the selected gene by an antibiotic deletion cassette. These cassettes including an oriT and an antibiotic resistance gene (aac(3)IV for apramycin resistance, Table 1), and flanked by FRT sites (FLP-recombinase recognition targets) were generated by PCR using primers with gene-specific homology extensions (Table 2), and pIJ773 (Table 1) as template. The gel-purified deletion cassettes were electroporated into the *E. coli* BW25113 strain harboring the arabinose-inducible λ RED expression plasmid, pIJ790, and cosmid 833 containing the gene of interest. Transformants were recovered on apramycin selective medium, and correct gene replacement in the cosmid was confirmed by PCR and sequencing. The resulting mutated cosmid was then transferred into *S. scabies* 87-22 via intergeneric conjugation after passage through the *E. coli* ET12567 strain harboring pUZ8002 (Table 1). Exconjugants were selected for resistance to apramycin, and sensitivity to kanamycin. Genomic DNA was extracted from *Streptomyces* cultures grown in TSB medium using the MasterPure™ Gram Positive DNA Purification Kit (Epicentre Biotechnologies) according to the manufacturer's instructions and verification of the mutant isolates was performed by PCR.

Analysis of Thaxtomin A Production

Mycelial suspensions of *S. scabies* strains were prepared from 48-72 h-old TSB-grown cultures by pelleting the mycelia, washing twice with sterile water, and resuspending in 1 ml sterile water to obtain an optical density at 600 nm ($OD_{600\ nm}$) of 1.0. For analysis of thaxtomin production, OBB medium (Johnson et al. 2007, incorporated herein by reference) as well as TDM medium with cellobiose or glucose as the only carbon source (modified from Johnson et al. 2007) was used. Three times 50 ml medium in 250 ml flasks were inoculated with 200 µl of mycelial suspension of $OD_{600\ nm}$ 1.0. After incubation for 7 days at 28±2° C. with shaking at ~250 rpm, a 10 ml culture sample was taken from each culture. Thaxtomin A was purified from the supernatant and analyzed by HPLC as described previously (Johnson et al. 2007). The pellets of the culture samples were dried and weighed as a measure for bacterial growth.

Samples of 50 µl from a mycelial suspension of $OD_{600\ nm}$ 1.0 were plated out on small petri dishes (5 cm diameter) containing 12.5 ml solid medium. After incubation for 7 days at 28° C., plates were visually inspected for thaxtomin production based on the typical yellow pigmentation due to secreted thaxtomin. Experiments were repeated using different biological replicates of the *Streptomyces* strains with three technical replicates per strain.

His-Tagged CebR Production in *E. coli* and Protein Purification

The orf encoding SCAB57761 was amplified by PCR using the primers SCAB_57761+3_NdeI and SCAB_57761+1056_EcoRI (Table 2). The corresponding PCR product was subsequently cloned into the pJET1.2/blunt Cloning Vector, yielding pSAJ001. After DNA sequencing, a NdeI-EcoRI DNA fragment was excised from pSAJ001 and cloned into pET-22b digested with the same restriction enzymes. The resulting construct, pSAJ002, was transformed to *E. coli* BL21(DE3) competent cells. *E. coli* cells carrying pSAJ002 were grown at 37° C. in 250 ml LB medium containing 100 µg/ml of ampicillin until the culture reached an optical density at 600 nm ($OD_{600}$) of 0.6. Production of $His_6$-tagged CebR was induced overnight (~20 h) at 16° C. by addition of 1 mM isopropyl-β-d-thiogalactopyranoside (IPTG). Cells were collected by centrifugation and ruptured by sonication in lysis buffer (50 mM Tris-HCl buffer; pH 7.5; supplemented with the Complete Protease Inhibitor Cocktail, EDTA-free, Roche). Soluble proteins were first loaded onto a pre-equilibrated $Ni^{2+}$-nitrilotriacetic acid (NTA)-agarose column (5 ml bed volume) to remove most of the *E. coli* proteins. The flow-through potentially containing proteins not bound during this first purification was reloaded onto a second Ni-NTA-agarose column. Both columns were washed with 25 ml of washing buffer (Tris-HCl 50 mM, NaCl 200 mM). $His_6$-tagged CebR was eluted at around 150 mM imidazole. Fractions containing the pure protein were pooled and desalted using a HiTrap Desalting column (GE Healthcare) with 20 mM Tris-HCl buffer.

Protein Identification by LC-ESI-MS/MS

The band containing the $His_6$-tagged CebR protein was excised from the SDS-PAGE gel stained with Coomassie Blue, reduced, alkylated and digested within the gel slice using trypsin. The protein digest was independently analyzed on a Liquid Chromatograph (nano Ultimate 3000-Dionex)—ESI-ion trap (AmaZon Speed EDT-Bruker Daltonics), in positive ion mode. Spectra were interpreted using Data analysis vs 4.0 (Bruker). Database searches were performed using the Mascot server vs. 2.2.04 and Protein Scape vs. 3.0 (Bruker) on NCBI, restricted to bacterial taxonomies.

Electromobility Gel Shift Assays (EMSAs)

EMSAs with 34-bp double-stranded probes (generated by PCR, Table 2) were performed using Cy5-labeled cbs probes (6 nM and 30 nM final concentration) and $His_6$-tagged CebR at a final concentration between 0.08 and 3.2 µM in a total reaction volume of 50 µl. All reactions were carried out in EMSA buffer (10 mM Tris-HCl, pH 7.5, 1 mM dithiothreitol [DTT], 0.25 mM $CaCl_2$, 0.5 mM $MgCl_2$, 50 mM KCl, and 2% glycerol) containing excess of nonspecific DNA (salmon sperm DNA). After 15 min of incubation at room temperature, reaction mixtures were loaded onto a 1% (wt/vol) agarose gel. Bound and unbound probes were separated by gel electrophoresis for 30 min at 100 V at room temperature, and fluorescent DNA was visualized using a Typhoon Trio+ variable-mode imager (FRFC 2.4506.08).

Real-Time Quantitative RT-PCR

RNA was prepared from 72-h old mycelia grown on ISP-4 plates at 28° C. using the RNeasy Mini Kit (Qiagen) according to the manufacturer's instructions. PCR reactions on the purified RNA were performed to verify the absence of genomic DNA. cDNA synthesis was performed on 1 µg of DNAse-treated (Turbo DNA-free Kit, Ambion) RNA using the iScript™ cDNA Synthesis Kit (BioRad). Quantitative Real-Time PCR (qPCR) was carried out in 10 µl containing 4 µl of SsoAdvanced™ Sybr® Green Supermix (BioRad), 4 µl of 1/10 diluted cDNA and 0.5 pmol of each gene-specific primer (Table 2), and subjected to the following PCR protocol: 3 min at 95° C., 40 cycles of 30 s at 95° C. followed by 45 s at 60° C. A melting curve analysis (samples were heated from 60° C. to 95° C.) was performed after each qPCR run to verify specific amplification. The murX, hrdB and gyrA genes (Joshi et al., 2007) were used to normalize the amount of RNA in the samples. Each measurement was performed in triplicate with three different cebR mutant isolates.

Example 2

The present example demonstrates that inactivation of bglC encoding the enzyme that hydrolyses cellobiose (the best allosteric effector of CebR) also results in a mutant strain that constitutively produces thaxtomin.

Deletion of the β-Glucosidase Gene Accompanying the Cellobiose/Cellotriose Transporter Upon active transport of cellobiose/cellotriose into the cell, catabolism of the incoming cellobiose is accomplished by a β-glucosidase that cleaves the β1→4 glycosidic bond linking the two glucose molecules. Deletion of the μ-glucosidase gene (scab57721) associated with the cellobiose/cellotriose-specific ABC transporter in *S. scabies* resulted in increased thaxtomin production on most of the media tested. The mutant overproduced thaxtomin in OBB cultures (FIG. 9A) as well as on OBA plates (FIG. 9B), while the addition of cellobiose did not increase the thaxtomin levels of the mutant compared to the wild type strain (FIG. 9B). Even on Thaxtomin Defined Medium (TDM, Johnson et al. 2007) with glucose as the only carbon source, the β-glucosidase deletion mutant produced up to 50% of wild type levels on TDM with cellobiose (FIG. 10). Overproduction was also measured on ISP-4. Moreover, addition of cellobiose to the ISP-4 medium further increased the thaxtomin production level of the β-glucosidase mutant (FIG. 11).

Materials and methods are as described above for Example 1. Generation of the bglC gene deletions in *S. scabies* 87-22 was performed as described above for the cebR gene deletions. Briefly, deletion mutants in *S. scabies* 87-22 were created using the REDIRECT PCR targeting methodology (Gust et al. 2003, incorporated herein by reference) replacing the selected gene by an antibiotic deletion cassette.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

Tables

TABLE 1

Bacterial strains, plasmids, and cosmids used in this study

| Strain or plasmid | Description† | Source or reference |
|---|---|---|
| *Streptomyces* strains | | |
| 87-22 (wild type) | *S. scabies* wild type strain | (Loria et al. 1995) |
| Δscab57761 (ΔcebR) | 87-22 derivative with a deletion of the scab57761 gene ($Apr^R$) | This study |
| Δscab57721 (Δβ-gluc) | 87-22 derivative with a deletion of the scab57721 gene ($Apr^R$) | This study |
| *E. coli* strains | | |
| Rosetta (DE3) | Host for heterologous expression of cebR from the pET-22b vector | Novagen |
| DH5α | General cloning host | Gibco-BRL |
| BW25113 | Host for the REDIRECT PCR targeting system | (Gust et al. 2003) |
| ET12567 | $dam^-$, $dcm^-$, $hsdS^-$; non-methylating host for transfer of DNA into *Streptomyces* spp. ($Cml^R$, $Tet^R$) | (MacNeil et al. 2003) |
| Plasmids or cosmids | | |
| pIJ790 | λ Red plasmid ($t^S$, $Cml^R$) | (Gust et al. 2003) |
| pUZ8002 | Supplies transfer functions for mobilization of oriT-containing vectors from *E. coli* to *Streptomyces* ($Kan^R$) | (Kieser et al. 2000) |
| pIJ773 | Template for the REDIRECT PCR targeting system, contains the [aac(3)IV + oriT] disruption cassette ($Amp^R$, $Apr^R$) | (Gust et al. 2003) |
| SuperCos1 | Cosmid cloning vector ($Amp^R$, $Kan^R$) | Stratagene |
| Cosmid 833 | SuperCos1 derivative containing the *S. scabies* 87-22 cellobiose/cellotriose-specific ABC-transporter locus ($Kan^R$, $Amp^R$) | This study |
| pJET1.2/blunt Cloning Vector | Plasmid used for efficient cloning of PCR products ($Amp^R$) | Thermo scientific |
| pSAJ001 | pJET1.2 derivative containing the *S. scabies* 87-22 cebR gene ($Amp^R$) | This study |
| pET-22b | Expression vector used for production of $His_6$-tagged CebR in *E. coli* BL21 (DE3). | Novagen |
| pSAJ002 | pET-22b derivative containing the *S. scabies* 87-22 cebR gene inserted into the NdeI-EcoRI sites ($Amp^R$) | This study |
| pAU3-45 | pSET152 (a ϕC31-derived integration vector) derivative containing the tsr gene inserted into the (blunted) NheI site ($Apr^R$, $Thio^R$) | (Bignell et al. 2005) |

TABLE 1-continued Bacterial strains, plasmids, and cosmids used in this study

| Strain or plasmid | Description[†] | Source or reference |
|---|---|---|
| pRLIF8 | pAU3-45 derivative containing the scab57761 gene and its promoter inserted into the XbaI site (Apr$^R$, Thio$^R$) | This study |

[†]Apr$^R$, apramycin resistance;
Cml$^R$, chloramphenicol resistance;
Tet$^R$, tetracyclin resistance;
t$^s$, temperature sensitive;
Kan$^R$, kanamycin resistance;
Amp$^R$, ampicillin resistance;
Thio$^R$, thiostrepton resistance

TABLE 2

List of oligonucleotides used in this study

| Primer | Sequence (5'→3')* (SEQ ID NO) | Use |
|---|---|---|
| imf196 | gattccacgccagcgcggtagtgacgggagac gaccatgattccggggatccgtcgacc (SEQ ID NO: 8) | scab57761 Redirect deletion cassette |
| imf197 | caagcgcttcgtcatccaggtcgatctgggtcgc actcatgtaggctggagctgcttc (SEQ ID NO: 9) | scab57761 Redirect deletion cassette |
| imf198 | ctcccacgagtgatgtgttg (SEQ ID NO: 10) | PCR verification of Δscab57761 |
| imf199 | ccgtgtccttcttcatggtg (SEQ ID NO: 11) | PCR verification of Δscab57761 |
| DRB21 | gtctggcagttccaggagtc (SEQ ID NO: 12) | murX gene expression analysis (qPCR) |
| DRB22 | aggtgttccaccacaggaag (SEQ ID NO: 13) | murX gene expression analysis (qPCR) |
| DRB23 | ggacatccagacgcagtaca (SEQ ID NO: 14) | gyrA gene expression analysis (qPCR) |
| DRB24 | Ctcggtgttgagcttctcct (SEQ ID NO: 15) | gyrA gene expression analysis (qPCR) |
| DRB9 | tggtcgaggtcatcaacaag (SEQ ID NO: 16) | hrdB gene expression analysis (qPCR) |
| DRB10 | tggacctcgatgaccttctc (SEQ ID NO: 17) | hrdB gene expression analysis (qPCR) |
| DRB13 | gagcgactgtccttcatgg (SEQ ID NO: 18) | txtA gene expression analysis (qPCR) |
| DRB14 | cgtcgtccagtaccacgag (SEQ ID NO: 19) | txtA gene expression analysis (qPCR) |
| DRB48 | cggctacttcccgatggat (SEQ ID NO: 20) | txtB gene expression analysis (qPCR) |
| DRB49 | ctcgatgtcactcctggtca (SEQ ID NO: 21) | txtB gene expression analysis (qPCR) |
| DRB60 | ggatgcgatccacttctgat (SEQ ID NO: 22) | txtR gene expression analysis (qPCR) |
| DRB61 | cgcaccgatatgttgtgttc (SEQ ID NO: 23) | txtR gene expression analysis (qPCR) |
| imf200 | ctgggttacgtcccgaacac (SEQ ID NO: 24) | scab57761 gene expression analysis (qPCR) |

TABLE 2-continued

List of oligonucleotides used in this study

| Primer | Sequence (5'→3')* (SEQ ID NO) | Use |
|---|---|---|
| imf201 | ccttgaggatgtcggagaag (SEQ ID NO: 25) | scab57761 gene expression analysis (qPCR) |
| imf274 | aaatctagaccagcgtgatcttggtcttg (SEQ ID NO: 26) | PCR complementation of Δscab57761 |
| imf275 | aaatctagaccgtgtccttcttcatggtg (SEQ ID NO: 27) | PCR complementation of Δscab57761 |
| imf304 | cgcgccccgtaacccgtcgcgcctatcgtgcgc cgggt<u>gattccggggatccgtcgacc</u> (SEQ ID NO: 28) | scab57721 Redirect deletion cassette |
| imf305 | ccacgcggggatgttgtgtgtgccgcaccggcc cggtc<u>atgtaggctggagctgcttc</u> (SEQ ID NO: 29) | scab57721 Redirect deletion cassette |
| imf306 | acttcttctggcccttcgtg (SEQ ID NO: 30) | PCR verification of Δscab57721 |
| imf307 | gcgggctcctacgactactg (SEQ ID NO: 31) | PCR verification of Δscab57721 |
| SCAB_57761 + 3_Ndei | catatggtgacaggccacggggc (SEQ ID NO: 32) | Cloning of scab57761 in pET-22b |
| SCAB_57761 + 1056_EcoRI | gaattcggaagaatcccgccccacc (SEQ ID NO: 33) | Cloning of scab57761 in pET-22b |
| SCAB_31791-909 Cy5 | tgtcaataagcgggagcgctcccacagcgctct c (SEQ ID NO: 34) | EMSA probe cbs$^{txtR-A}$ |
| SCAB_31801-796 | gagagcgctgtgggagcgctcccgcttattgac a (SEQ ID NO: 35) | EMSA probe cbs$^{txtR-A}$ |
| SCAB_57751c-140 Cy5 | ccaggtactgtgggagcgctcccacgagtgatg t (SEQ ID NO: 36) | EMSA probe cbs$^{cebR-E}$ |
| SCAB_57761-506 | acatcactcgtgggagcgctcccacagtacctg g (SEQ ID NO: 37) | EMSA probe cbs$^{cebR-E}$ |
| SCAB_31781c + 1530 Cy5 | ctcccccaggggagcgctcccactgcgctgta (SEQ ID NO: 38) | EMSA probe cbs$^{txtB}$ |
| SCAB_31781c + 1497 | tacagcgcagtgggagcgctcccccctggggga g (SEQ ID NO: 39) | EMSA probe cbs$^{txtB}$ |
| SCAB_57721 + 10 | ggttcaggcatggaagcgctcccattggtggtc g (SEQ ID NO: 40) | EMSA probe cbs$^{bglC}$ |
| SCAB_57721-24_Cy5 | cgaccaccaatgggagcgcttccatgcctgaa cc (SEQ ID NO: 41) | EMSA probe cbs$^{bglC}$ |

*Non-homologous extensions are underlined, while engineered restriction sites are indicated in bold.

Additional Nucleic Acid and Protein Sequences cebR (scab57761)
(SEQ ID NO: 1)
ATGGTGACAGGCCACGGGGCACGGGGCCGGAGCGGTGGGCGGCCGACGTT

GGAGGAGGTCGCCGCACGGGCCGGAGTGGGCCGGGGGACGGTGTCCCGGG

TGATCAACGGCTCGCCCCGGGTGAGCGACGCGACCCGCGCGGCGGTCGAG

GCGGCCGTCGCGGAGCTGGGTTACGTCCCGAACACGGCGGCCCGCGCGCT

CGCGGCGAACCGTACCGACGCGATCGCGATGGTCGTGCCCGAACCGGAGA

CCCGCTTCTTCTCGGAGCCGTACTTCTCCGACATCCTCAAGGGTGTCGGA

GCGCAACTGTCCGACACCGAGATGCAGCTCCTGCTGATCTTCGCGGGCAA

CGACCGGGAGCGCCGGCGCCTCGCCCAGTACCTGGCCGCGCACCGCGTCG

ACGGTGTCCTCCTGGTCTCCGTCCACGCGGACGACCCGCTCCCCGATCTG

CTGTCGCAACTGGAAATCCCGGCCGTCATCAGCGGCCCCCGCTCCGAGCA

CGAGACGCTCCCCTCGGTCGACTCCGACAACTACGGCGGCGGCCGCTCGG

CGGTCGAGCACCTCATCGCACGGGGCGCGCCCGGATCGCCACGATCACC

GGCCGGCTGGACGTCTACGGCGCCCAGCGGCGCATCGAGGGCTACCGCGA

CGCCCTGGAGGACGCGGGCCGCGAGGTGGACGAGCGCCTGATCGCCCCCG

GTGACTTCACGGAGGAGGGCGGCCGCCGAGCGATGCGCGAACTCCTGGCC

CGCTGCCCCGACCTCGACGCGGTCTTCGCCGAGTCGGACGTCATGGCCGC

CGGCGCCCGCCAGGTGCTCCGCGAGGAGGGCCGCCGCATACCCGACGACG

TGGCGCTGGTCGGCTACGACGACTCGGCGATCGCCCGCCACATGGACCCG

CCGCTCACCAGCGTCCGCCAGCCGATAGAGGAGATGGGCCGCGCGATGAT

CGACCTCCTCCTGGACGAGATCGCGGACCGCCGCCCGGCGGTGTCGAGGG

GCTTGGAACGACGCCAGGTGGTGCTGCCGACGGAGCTGGTGGGGCGGGAT

TCTTCCTGA

CebR (SCAB57761)

(SEQ ID NO: 2)

MVTGHGARGRSGGRPTLEEVAARAGVGRGTVSRVINGSPRVSDATRAAVE

AAVAELGYVPNTAARALAANRTDAIAMVVPEPETRFFSEPYFSDILKGVG

AQLSDTEMQLLLIFAGNDRERRRLAQYLAAHRVDGVLLVSVHADDPLPDL

LSQLEIPAVISGPRSEHETLPSVDSDNYGGGRSAVEHLIARGRARIATIT

GRLDVYGAQRRIEGYRDALEDAGREVDERLIAPGDFTEEGGRRAMRELLA

RCPDLDAVFAESDVMAAGARQVLREEGRRIPDDVALVGYDDSAIARHMDP

PLTSVRQPIEEMGRAMIDLLLDEIADRRPAVSRGLERRQVVLPTELVGRD

SS bglC (scab57721)

(SEQ ID NO: 3)

ATGCCTGAACCCGTGAATCCGGCCACCCCGGTGACCTTTCCTCCCGCCTT

CCTCTGGGGCGCGGCCACCTCCGCGTACCAGATCGAGGGGGCGGTGCGGG

AGGACGGCCGTACGCCCTCCATCTGGGACACCTTCAGTCACACGCCGGGC

AAGACCGCCGGCGGCGAGAACGGTGACATCGCTGTCGACCACTACCACCG

CTACCGCGACGACTGGCGATGATGGCGGACCTGGGCCTCAACGCGTACC

GCTTCTCCGTCTCCTGGTCGCGGGTGCAGCCGACGGGGCGGGGCCCGGCC

GTCCAGAAGGGGCTCGACTTCTACCGACGGCTGGTCGACGAGCTGCTGGC

CAAGGGCATCAAGCCCGCCGTCACCCTCTACCACTGGGACCTCCCGCAGG

AGCTGGAGGACGCCGGCGGCTGGCCCGAGCGGGACATCGTGCACCGGTTC

GCCGAGTACGCGCGGATCATGGGCGAGGCGCTCGGCGACCGCGTCGAGCA

GTGGATCACCCTCAACGAGCCGTGGTGCACCGCGTTCCTGGGCTACGGCT

CCGGGGTGCACGCGCCGGGCCGTACGGACCCGGTGGCGTCCCTGCGCGCG

GCCCACCATCTGAACGTGGCGCACGGCCTCGGCGTCTCGGCGCTGCGGTC

GGCGATGCCCGCCCGCAACTCGATCGCGGTGAGCCTCAACTCCTCGGTGG

TGCGGCCGATCACCAGCTCCCCGGAGGACCGGGCGCGCGGCCCGGAAGATC

GACGACCTCGCGAACGGCGTCTTCCACGGACCGATGCTGCACGGGGCCTA

CCCCGAGACCCTGTTCGCCGCGACCTCGTCGCTGACGGACTGGTCGTTCG

TGCGGGACGGTGACGTGGCGACGGCCCATCAGCCGCTGGACGCTCTGGGG

CTGAACTACTACACGCCGGCGCTGGTCGGCGCGGCGGACGCCGGCCTGGA

GGGCCCCCGCGCGGACGGCCACGGGGCGAGCGAGCACTCGCCGTGGCCGG

CCGCGGACGACGTCCTGTTCCACCAGACCCCGGGCGAGCGTACGGAGATG

GGCTGGACCATCGACCCGACGGGCCTGCACGAGCTGATCATGCGGTACGC

GCGGGAGGCTCCGGGCCTGCCGATGTACGTGACGGAGAACGGCGCCGTAC

GACGACAAGATGGACGCGGACGGCCGTGTCCACGACCCCGAGCGCATC

GCCTACCTGCACGGCCACCTGCGGGCGGTCCGGCGCGCGATCGCCGAGGG

GGCGGACGTGCGCGGGTACTACCTGTGGTCCCTGATGGACAACTTCGAGT

GGGCGTACGGCTACGGCAAGCGCTTCGGCGCGGTGTACGTCGACTACGCG

ACCCTGACCCGCACACCGAAGTCGAGCGCGCACTGGTACGGGCAGGCGGC

GAAGACGGGCGCCCTCCCGCCGCTGGCGCCGGCGCCGGCGTAG

BglC (SCAB57721)

(SEQ ID NO: 4)

MPEPVNPATPVTFPPAFLWGAATSAYQIEGAVREDGRTPSIWDTFSHTPG

KTAGGENGDIAVDHYHRYRDDVAMMADLGLNAYRFSVSWSRVQPTGRGPA

VQKGLDFYRRLVDELLAKGIKPAVTLYHWDLPQELEDAGGWPERDIVHRF

AEYARIMGEALGDRVEQWITLNEPWCTAFLGYGSGVHAPGRTDPVASLRA

AHHLNVAHGLGVSALRSAMPARNSIAVSLNSSVVRPITSSPEDRAAARKI

DDLANGVFHGPMLHGAYPETLFAATSSLTDWSFVRDGDVATAHQPLDALG

LNYYTPALVGAADAGLEGPRADGHGASEHSPWPAADDVLFHQTPGERTEM

GWTIDPTGLHELIMRYAREAPGLPMYVTENGAAYDDKMDADGRVHDPERI

AYLHGHLRAVRRAIAEGADVRGYYLWSLMDNFEWAYGYGKRFGAVYVDYA

TLTRTPKSSAHWYGQAAKTGALPPLAPAPA

Apramycin resistance gene deletion cassette (SEQ ID NO: 42)

ATTCCGGGGATCCGTCGACCTGCAGTTCGAAGTTCCTATTCTCTAGAAAG

TATAGGAACTTCGAAGTTCCCGCCAGCCTCGCAGAGCAGGATTCCCGTTG

AGCACCGCCAGGTGCGAATAAGGGACAGTGAAGAAGGAACACCCGCTCGC

GGGTGGGCCTACTTCACCTATCCTGCCCGGCTGACGCCGTTGGATACACC

AAGGAAAGTCTACACGAACCCTTTGGCAAAATCCTGTATATCGTGCGAAA

AAGGATGGATATACCGAAAAAATCGCTATAATGACCCCGAAGCAGGGTTA

TGCAGCGGAAAATGCAGCTCACGGTAACTGATGCCGTATTTGCAGTACCA

GCGTACGGCCCACAGAATGATGTCACGCTGAAAATGCCGGCCTTTGAATG

GGTTCATGTGCAGCTCCATCAGCAAAAGGGGATGATAAGTTTATCACCAC

CGACTATTTGCAACAGTGCCGTTGATCGTGCTATGATCGACTGATGTCAT

CAGCGGTGGAGTGCAATGTCGTGCAATACGAATGGCGAAAAGCCGAGCTC

ATCGGTCAGCTTCTCAACCTTGGGGTTACCCCCGGCGGTGTGCTGCTGGT

CCACAGCTCCTTCCGTAGCGTCCGGCCCCTCGAAGATGGGCCACTTGGAC

TGATCGAGGCCCTGCGTGCTGCGCTGGGTCCGGGAGGGACGCTCGTCATG

CCCTCGTGGTCAGGTCTGGACGACGAGCCGTTCGATCCTGCCACGTCGCC

CGTTACACCGGACCTTGGAGTTGTCTCTGACACATTCTGGCGCCTGCCAA

ATGTAAAGCGCAGCGCCCATCCATTTGCCTTTGCGGCAGCGGGGCCACAG

GCAGAGCAGATCATCTCTGATCCATTGCCCCTGCCACCTCACTCGCCTGC

AAGCCCGGTCGCCCGTGTCCATGAACTCGATGGGCAGGTACTTCTCCTCG

GCGTGGGACACGATGCCAACACGACGCTGCATCTTGCCGAGTTGATGGCA

AAGGTTCCCTATGGGGTGCCGAGACACTGCACCATTCTTCAGGATGGCAA

GTTGGTACGCGTCGATTATCTCGAGAATGACCACTGCTGTGAGCGCTTTG

CCTTGGCGGACAGGTGGCTCAAGGAGAAGAGCCTTCAGAAGGAAGGTCCA

```
-continued
GTCGGTCATGCCTTTGCTCGGTTGATCCGCTCCCGCGACATTGTGGCGAC

AGCCCTGGGTCAACTGGGCCGAGATCCGTTGATCTTCCTGCATCCGCCAG

AGGCGGGATGCGAAGAATGCGATGCCGCTCGCCAGTCGATTGGCTGAGCT

CATAAGTTCCTATTCCGAAGTTCCTATTCTCTAGAAAGTATAGGAACTTC

GAAGCAGCTCCAGCCTACA
```

REFERENCES

Barry, S. M., Kers, J. A., Johnson, E. G., Song, L., Aston, P. R., Patel, B., Krasnoff, S. B., Crane, B. R., Gibson, D. M., Loria, R. and Challis, G. L. 2012. Cytochrome P450-catalyzed L-tryptophan nitration in thaxtomin phytotoxin biosynthesis. Nat. Chem. Biol. 8(10): 814-816.

Bignell, D. R., Francis, I. M., Fyans, J. and Loria, R. 2014. Thaxtomin A production and virulence are controlled by several bld gene global regulators in Streptomyces scabies. Mol. Plant Microbe Interact. 27(8): 875-885.

Bignell, D. R., Tahlan, K., Colvin, K. R., Jensen, S. E. and Leskiw, B. K. 2005. Expression of ccaR, encoding the positive activator of cephamycin C and clavulanic acid production in Streptomyces clavuligerus, is dependent on bldG. Antimicrob. Agents Chemother. 49: 1529-1541.

Bischoff, V., Cookson, S. J., Wu, S. and Scheible, W. R. 2009. Thaxtomin A affects CESA-complex density, expression of cell wall genes, cell wall composition, and causes ectopic lignification in Arabidopsis thaliana seedlings. J. Exp. Bot. 60(3): 955-965.

Craig, M., Lambert, S., Jourdan, S., Tenconi, E., Colson, S., Maciejewska, M., Ongena, M., Martin, J. F., van Wezel, G. and Rigali, S. 2012. Unsuspected control of siderophore production by N-acetylglucosamine in streptomycetes. Environ. Microbiol. Rep. 4(5): 512-521.

Guan, D., Grau, B. L., Clark, C. A., Taylor, C. M., Loria, R. and Pettis, G. S. 2012. Evidence that thaxtomin C is a pathogenicity determinant of Streptomyces ipomoeae, the causative agent of Streptomyces soil rot disease of sweet potato. Mol. Plant Microbe Interact. 25(3): 393-401.

Gust, B., Challis, G. L., Fowler, K., Kieser, T. and Chater, K. F. 2003. PCR-targeted Streptomyces gene replacement identifies a protein domain needed for biosynthesis of the sesquiterpene soil odor geosmin. Proc. Natl. Acad. Sci. U.S.A. 100: 1541-1546.

Hiard, S., Maree, R., Colson, S., Hoskisson, P. A., Titgemeyer, F., van Wezel, G. P., Joris, B., Wehenkel, L. and Rigali, S. 2007. PREDetector: a new tool to identify regulatory elements in bacterial genomes. Biochem. Biophys. Res. Commun. 357(4): 861-864.

Heim, D. R., Skomp, J. R., Tschabold, E. E and Larrinua, I. M. 1990. Isoxaben inhibits synthesis of acid insoluble cell wall materials in Arabidopsis thaliana. Plant Physiol. 93: 695-700.

Hopwood, D. A. 2007. How do antibiotic-producing bacteria ensure their self-resistance before antibiotic biosynthesis incapacitates them? Mol. Microbiol. 63(4): 937-940.

Johnson, E. G., Joshi, M. V., Gibson, D. M. and Loria, R. 2007. Cello-oligosaccharides released from host plants induce pathogenicity in scab-causing Streptomyces species. Physiol. Mol. Plant Pathol. 71: 18-25.

Johnson, E. G., Krasnoff, S. B., Bignell, D. R., Chung, W. C., Tao, T., Parry, R. J., Loria, R. and Gibson, D. M. 2009. 4-Nitrotryptophan is a substrate for the non-ribosomal peptide synthetase TxtB in the thaxtomin A biosynthetic pathway. Mol. Microbiol. 73(3): 409-418.

Joshi, M. V., Bignell, D. R., Johnson, E. G., Sparks, J. P., Gibson, D. M. and Loria, R. 2007. The AraC/XylS regulator TxtR modulates thaxtomin biosynthesis and virulence in Streptomyces scabies. Mol. Microbiol. 66(3): 633-642.

Kieser, T., Bibb, M. J., Buttner, M. J., Chater, K. F. and Hopwood, D. A. 2000. Practical Streptomyces genetics. Norwich, UK, The John Innes Foundation.

King, R. R., Lawrence, C. H. and Gray, J. A. 2001. Herbicidal properties of the thaxtomin group of phytotoxins. J. Agric. Food Chem. 49(5): 2298-2301.

Lauzier, A., Simao-Beaunoir, A. M., Bourassa, S., Poirier, G. G., Talbot, B. and Beaulieu, C. 2008. Effect of potato suberin on Streptomyces scabies proteome. Mol. Plant Pathol. 9(6): 753-762.

Loria, R., Bignell, D. R., Moll, S., Huguet-Tapia, J. C., Joshi, M. V., Johnson, E. G., Seipke, R. F. and Gibson, D. M. 2008. Thaxtomin biosynthesis: the path to plant pathogenicity in the genus Streptomyces. Antonie van Leeuwenhoek 94(1): 3-10.

Loria, R., Bukhalid, R., Creath, R. and Olivier, M. 1995. Differential production of thaxtomins by pathogenic Streptomyces species in vitro. Biochem. Cell. Biol. 85(5): 537-541.

Loria, R., Kers, J. and Joshi, M. V. 2006. Evolution of plant pathogenicity in Streptomyces. Annu. Rev. Phytopathol. 44: 469-487.

MacNeil, D., Gewain, K., Ruby, C. and Dezeny, G. 1992. Analysis of Streptomyces avermitilis genes required for avermectin biosynthesis utilizing a novel integration vector. Gene 111(1): 61-68.

Marrone Bio Innovations, Inc. (2009) Uses of thaxtomin and thaxtomin compositions as herbicides. http://www.google.com/patents/US20100167930.

Marrone Bio Innovations, Inc. (2010) Use of thaxtomin for selective control of rice and aquatic based weeds. http://www.google.com/patents/US20100267560.

Marushima, K., Ohnishi, Y. and Horinouchi, S. 2009. CebR as the master regulator for cellulose/cellooligosaccharide catabolism affects morphological development in Streptomyces griseus. J. Bacteriol. 191(19): 5930-5940.

Novozymes Biologicals, Inc. (2011) Methods of controlling algae with thaxtomin and thaxtomin compositions. http://www.google.com/patents/EP2520167A1?cl=en.

Novozymes Biologicals, Inc. (2012) Methods of controlling weeds with thaxtomin and thaxtomin compositions in combination with a beneficial herbicide. http://www.google.com/patents/WO2013066894A3?cl=en.

Scheible, W. R., Fry, B., Kochevenko, A., Schindelasch, D., Zimmerli, L., Somerville, S., Loria, R. and Somerville, C. R. 2003. An Arabidopsis mutant resistant to thaxtomin A, a cellulose synthesis inhibitor from Streptomyces scabies. Plant Cell 15(8): 1781-1794.

Schlösser, A., Aldekamp, T. and Schrempf, H. 2000. Binding characteristics of CebR, the regulator of the ceb operon required for cellobiose/cellotriose uptake in Streptomyces reticuli. FEMS Microbiol. Lett. 190(1): 127-132.

Schlösser, A., Kampers, T. and Schrempf, H. 1997. The Streptomyces ATP-binding component MsiK assists in cellobiose and maltose transport. J. Bacteriol. 179(6): 2092-2095.

Wach, M. J., Krasnoff, S. B., Loria, R. and Gibson, D. M. 2007. Effect of carbohydrates on the production of thaxtomin A by Streptomyces acidiscabies. Arch. Microbiol. 188(1): 81-88.

We claim:

1. A genetically modified *Streptomyces* bacterium comprising:

a mutation that reduces activity of a β-glucosidase enzyme encoded by a bglC gene, such that the genetically modified *Streptomyces* has increased production of a thaxtomin compound as compared to a corresponding wild type *Streptomyces* bacterium.

2. The genetically modified *Streptomyces* bacterium of claim 1, wherein the mutation is a mutation of a native bglC gene, wherein the mutation reduces production or functionality of a β-glucosidase enzyme encoded by the bglC gene.

3. The genetically modified *Streptomyces* bacterium of claim 2, wherein the mutation of bglC is a null mutation.

4. The genetically modified *Streptomyces* bacterium of claim 1, wherein the bacterium does not produce functional β-glucosidase enzyme encoded by the bglC gene.

5. The genetically modified *Streptomyces* bacterium of claim 1, wherein the mutation comprises an exogenous nucleic acid sequence introduced into the bacterium, wherein the exogenous nucleic acid sequence reduces activity of a β-glucosidase enzyme encoded by the bglC gene.

6. The genetically modified *Streptomyces* bacterium of claim 1, wherein the bglC gene has a nucleotide sequence of SEQ ID NO: 3 or a nucleotide sequence having about 80% or more sequence identity with SEQ ID NO: 3.

7. The genetically modified *Streptomyces* bacterium of claim 1, wherein the genetically modified *Streptomyces* bacterium is selected from the group of *Streptomyces* species consisting of: *Streptomyces scabies, Streptomyces acidiscabies*, and *Streptomyces turgidiscabies*.

8. A method of increasing production of a thaxtomin compound in a *Streptomyces* bacterium, the method comprising:

providing a *Streptomyces* bacterium from a species capable of producing one or more thaxtomin compounds under standard thaxtomin-inducing conditions;

genetically modifying the *Streptomyces* bacterium by creating a mutation in the bacterium, wherein the mutation reduces activity of a β-glucosidase enzyme encoded by a bglC gene, such that the genetically modified *Streptomyces* has increased production of a thaxtomin compound as compared to a corresponding wild type *Streptomyces* bacterium.

9. The method of claim 8, wherein the mutation is a mutation of a native bglC gene, wherein the mutation reduces production or functionality of a β-glucosidase enzyme encoded by the bglC gene.

10. The method of claim 9, wherein the mutation of bglC is a null mutation created by inserting a deletion cassette into the bglC gene to inhibit production of β-glucosidase.

11. The method of claim 8, wherein the mutation comprises an exogenous nucleic acid sequence introduced into the bacterium, wherein the exogenous nucleic acid sequence reduces activity of a β-glucosidase enzyme encoded by the bglC gene.

12. A method of increasing production of a thaxtomin compound in a *Streptomyces* bacterium, the method comprising suppressing the activity of a β-glucosidase enzyme encoded by a bglC gene.

13. The method of claim 12, wherein suppressing the activity of the β-glucosidase enzyme comprises genetically modifying the *Streptomyces* bacterium to inhibit expression of the bglC gene encoding the β-glucosidase enzyme.

14. The method of claim 12, wherein suppressing the activity of the β-glucosidase enzyme comprises genetically modifying the *Streptomyces* bacterium to introduce an exogenous nucleic acid sequence, wherein the exogenous nucleic acid sequence reduces activity of the β-glucosidase enzyme encoded by the bglC gene.

15. The method of claim 12, wherein the bglC gene has a nucleotide sequence of SEQ ID NO: 3 or a sequence having about 80% or more sequence identity with SEQ ID NO: 3.

16. A method of producing a thaxtomin compound, the method comprising:

culturing genetically modified *Streptomyces* bacteria, wherein the genetically modified *Streptomyces* bacteria comprise a mutation of a native bglC gene, wherein the mutation reduces production or functionality of a β-glucosidase enzyme encoded by the bglC gene, such that the modified *Streptomyces* bacteria have increased production of a thaxtomin compound as compared to a corresponding wild type *Streptomyces* bacteria.

17. The method of claim 16, further comprising extracting the thaxtomin compound from the culture media.

18. The method of claim 16, further comprising culturing the genetically modified *Streptomyces* bacteria in a culture medium that does not contain cellobiose, wherein the genetically modified *Streptomyces* bacteria are capable of producing a thaxtomin compound in the absence of cellobiose.

* * * * *

SEQUENCE LISTING

<160> NUMBER OF SEQ ID NOS: 43

<210> SEQ ID NO 1
<211> LENGTH: 1059
<212> TYPE: DNA
<213> ORGANISM: Streptomyces scabies

<400> SEQUENCE: 1

```
atggtgacag gccacggggc acggggccgg agcggtgggc ggccgacgtt ggaggaggtc      60
gccgcacggg ccggagtggg ccggggacg gtgtcccggg tgatcaacgg ctcgccccgg      120
gtgagcgacg cgacccgcgc ggcggtcgag gcggccgtcg cggagctggg ttacgtcccg     180
aacacggcgg cccgcgcgct cgcggcgaac cgtaccgacg cgatcgcgat ggtcgtgccc     240
gaaccggaga cccgcttctt ctcggagccg tacttctccg acatcctcaa gggtgtcgga     300
gcgcaactgt ccgacaccga gatgcagctc ctgctgatct tcgcgggcaa cgaccgggag     360
cgccggcgcc tcgcccagta cctggccgcg caccgcgtcg acgtgtcct cctggtctcc     420 gtccacgcgg acgacccgct ccccgatctg ctgtcgcaac tggaaatccc ggccgtcatc     480
agcggccccc gctccgagca cgagacgctc ccctcggtcg actccgacaa ctacggcggc     540
ggccgctcgg cggtcgagca cctcatcgca cgggggcgcg cccggatcgc cacgatcacc     600
ggccggctgg acgtctacgg cgcccagcgg cgcatcgagg gctaccgcga cgccctggag     660
gacgcgggcc gcgaggtgga cgagcgcctg atcgcccccg gtgacttcac ggaggagggc     720
ggccgccgag cgatgcgcga actcctggcc cgctgccccg acctcgacgc ggtcttcgcc     780
gagtcggacg tcatggccgc cggcgcccgc caggtgctcc gcgaggaggg ccgccgcata     840
cccgacgacg tggcgctggt cggctacgac gactcggcga tcgcccgcca catggacccg     900
ccgctcacca gcgtccgcca gccgatagag gagatgggcc gcgcgatgat cgacctcctc     960
ctggacgaga tcgcggaccg ccgcccggcg gtgtcgaggg gcttggaacg acgccaggtg    1020
gtgctgccga cggagctggt ggggcgggat tcttcctga                           1059
```

<210> SEQ ID NO 2
<211> LENGTH: 352
<212> TYPE: PRT
<213> ORGANISM: Streptomyces scabies

<400> SEQUENCE: 2

```
Met Val Thr Gly His Gly Ala Arg Gly Arg Ser Gly Gly Arg Pro Thr
1               5                   10                  15

Leu Glu Glu Val Ala Ala Arg Ala Gly Val Gly Arg Gly Thr Val Ser
            20                  25                  30

Arg Val Ile Asn Gly Ser Pro Arg Val Ser Asp Ala Thr Arg Ala Ala
        35                  40                  45

Val Glu Ala Ala Val Ala Glu Leu Gly Tyr Val Pro Asn Thr Ala Ala
    50                  55                  60

Arg Ala Leu Ala Ala Asn Arg Thr Asp Ala Ile Ala Met Val Val Pro
65                  70                  75                  80

Glu Pro Glu Thr Arg Phe Phe Ser Glu Pro Tyr Phe Ser Asp Ile Leu
                85                  90                  95

Lys Gly Val Gly Ala Gln Leu Ser Asp Thr Glu Met Gln Leu Leu Leu
            100                 105                 110

Ile Phe Ala Gly Asn Asp Arg Glu Arg Arg Leu Ala Gln Tyr Leu
        115                 120                 125
```

```
Ala Ala His Arg Val Asp Gly Val Leu Leu Val Ser Val His Ala Asp
    130                 135                 140
Asp Pro Leu Pro Asp Leu Leu Ser Gln Leu Glu Ile Pro Ala Val Ile
145                 150                 155                 160
Ser Gly Pro Arg Ser Glu His Glu Thr Leu Pro Ser Val Asp Ser Asp
                165                 170                 175
Asn Tyr Gly Gly Gly Arg Ser Ala Val Glu His Leu Ile Ala Arg Gly
            180                 185                 190
Arg Ala Arg Ile Ala Thr Ile Thr Gly Arg Leu Asp Val Tyr Gly Ala
        195                 200                 205
Gln Arg Arg Ile Glu Gly Tyr Arg Asp Ala Leu Glu Asp Ala Gly Arg
210                 215                 220
Glu Val Asp Glu Arg Leu Ile Ala Pro Gly Asp Phe Thr Glu Glu Gly
225                 230                 235                 240
Gly Arg Arg Ala Met Arg Glu Leu Leu Ala Arg Cys Pro Asp Leu Asp
                245                 250                 255
Ala Val Phe Ala Glu Ser Asp Val Met Ala Ala Gly Ala Arg Gln Val
            260                 265                 270
Leu Arg Glu Glu Gly Arg Arg Ile Pro Asp Asp Val Ala Leu Val Gly
        275                 280                 285
Tyr Asp Asp Ser Ala Ile Ala Arg His Met Asp Pro Pro Leu Thr Ser
290                 295                 300
Val Arg Gln Pro Ile Glu Gly Met Gly Arg Ala Met Ile Asp Leu Leu
305                 310                 315                 320
Leu Asp Glu Ile Ala Asp Arg Arg Pro Ala Val Ser Arg Gly Leu Glu
                325                 330                 335
Arg Arg Gln Val Val Leu Pro Thr Glu Leu Val Gly Arg Asp Ser Ser
            340                 345                 350

<210> SEQ ID NO 3
<211> LENGTH: 1443
<212> TYPE: DNA
<213> ORGANISM: Streptomyces scabies

<400> SEQUENCE: 3
atgcctgaac ccgtgaatcc ggccaccccg gtgacctttc ctcccgcctt cctctggggc        60
gcggccacct ccgcgtacca gatcgagggg gcggtgcggg aggacggccg tacgccctcc       120
atctgggaca ccttcagtca cacgccgggc aagaccgccg gcggcgagaa cggtgacatc       180
gctgtcgacc actaccaccg ctaccgcgac gacgtggcga tgatggcgga cctgggcctc       240
aacgcgtacc gcttctccgt ctcctggtcg cgggtgcagc cgacggggcg gggcccggcc       300
gtccagaagg ggctcgactt ctaccgacgg ctggtcgacg agctgctggc caagggcatc       360
aagcccgccg tcaccctcta ccactgggac ctcccgcagg agctggagga cgccggcggc       420
tggcccgagc gggacatcgt gcaccggttc gccgagtacg cgcggatcat gggcgaggcg       480
ctcggcgacc gcgtcgagca gtggatcacc ctcaacgagc cgtggtgcac cgcgttcctg       540
ggctacggct ccggggtgca cgcgccgggc cgtacggacc cggtggcgtc cctgcgcgcg       600
gccaccatcc tgaacgtggc gcacggcctc ggcgtctcgg cgctgcggtc ggcgatgccc       660
gcccgcaact cgatcgcggt gagcctcaac tcctcggtgg tgcggccgat caccagctcc       720
ccggaggacc gggccgcggc ccggaagatc gacgacctcg cgaacggcgt cttccacgga       780
ccgatgctgc acgggccgta cccggagacc ctgttcgccg cgacctcgtc gctgacggac       840
tggtcgttcg tgcgggacgg tgacgtggcg acggccatca gccgctggaa cgctctgggg       900
```

-continued

```
ctgaactact acacgccggc gctggtcggc gcggcggacg ccggcctgga gggcccccgc   960
gcggacggcc acggggcgag cgagcactcg ccgtggccgg ccgcggacga cgtcctgttc  1020
caccagaccc cgggcgagcg tacggagatg ggctggacca tcgacccgac gggcctgcac  1080
gagctgatca tgcggtacgc gcgggaggct ccgggcctgc cgatgtacgt gacggagaac  1140
ggcgccgcgt acgacgacaa gatggacgcg gacggccgtg tccacgaccc cgagcgcatc  1200
gcctacctgc acggccacct gcgggcggtc cggcgcgcga tcgccgaggg gcggacgtg   1260
cgcgggtact acctgtggtc cctgatggac aacttcgagt gggcgtacgg ctacggcaag  1320
cgcttcggcg cggtgtacgt cgactacgcg accctgaccc gcacaccgaa gtcgagcgcg  1380
cactggtacg ggcaggcggc gaagacgggc gccctcccgc cgctggcgcc ggcgccggcg  1440
tag                                                                1443
```

<210> SEQ ID NO 4
<211> LENGTH: 480
<212> TYPE: PRT
<213> ORGANISM: Streptomyces scabies

<400> SEQUENCE: 4

```
Met Pro Glu Pro Val Asn Pro Ala Thr Pro Val Thr Phe Pro Pro Ala
1               5                   10                  15

Phe Leu Trp Gly Ala Ala Thr Ser Ala Tyr Gln Ile Glu Gly Ala Val
            20                  25                  30

Arg Glu Asp Gly Arg Thr Pro Ser Ile Trp Asp Thr Phe Ser His Thr
        35                  40                  45

Pro Gly Lys Thr Ala Gly Gly Glu Asn Gly Asp Ile Ala Val Asp His
    50                  55                  60

Tyr His Arg Tyr Arg Asp Asp Val Ala Met Met Ala Asp Leu Gly Leu
65                  70                  75                  80

Asn Ala Tyr Arg Phe Ser Val Ser Trp Ser Arg Val Gln Pro Thr Gly
                85                  90                  95

Arg Gly Pro Ala Val Gln Lys Gly Leu Asp Phe Tyr Arg Arg Leu Val
            100                 105                 110

Asp Glu Leu Leu Ala Lys Gly Ile Lys Pro Ala Val Thr Leu Tyr His
        115                 120                 125

Trp Asp Leu Pro Gln Glu Leu Glu Asp Ala Gly Gly Trp Pro Glu Arg
    130                 135                 140

Asp Ile Val His Arg Phe Ala Glu Tyr Ala Arg Ile Met Gly Glu Ala
145                 150                 155                 160

Leu Gly Asp Arg Val Glu Gln Trp Ile Thr Leu Asn Glu Pro Trp Cys
                165                 170                 175

Thr Ala Phe Leu Gly Tyr Gly Ser Gly Val His Ala Pro Gly Arg Thr
            180                 185                 190

Asp Pro Val Ala Ser Leu Arg Ala Ala His His Leu Asn Val Ala His
        195                 200                 205

Gly Leu Gly Val Ser Ala Leu Arg Ser Ala Met Pro Ala Arg Asn Ser
    210                 215                 220

Ile Ala Val Ser Leu Asn Ser Ser Val Val Arg Pro Ile Thr Ser Ser
225                 230                 235                 240

Pro Glu Asp Arg Ala Ala Ala Arg Lys Ile Asp Asp Leu Ala Asn Gly
                245                 250                 255

Val Phe His Gly Pro Met Leu His Gly Ala Tyr Pro Glu Thr Leu Phe
            260                 265                 270
```

-continued

```
Ala Ala Thr Ser Ser Leu Thr Asp Trp Ser Phe Val Arg Asp Gly Asp
            275                 280                 285

Val Ala Thr Ala His Gln Pro Leu Asp Ala Leu Gly Leu Asn Tyr Tyr
290                 295                 300

Thr Pro Ala Leu Val Gly Ala Ala Asp Ala Gly Leu Glu Gly Pro Arg
305                 310                 315                 320

Ala Asp Gly His Gly Ala Ser Glu His Ser Pro Trp Pro Ala Ala Asp
                325                 330                 335

Asp Val Leu Phe His Gln Thr Pro Gly Glu Arg Thr Glu Met Gly Trp
                340                 345                 350

Thr Ile Asp Pro Thr Gly Leu His Glu Leu Ile Met Arg Tyr Ala Arg
355                 360                 365

Glu Ala Pro Gly Leu Pro Met Tyr Val Thr Glu Asn Gly Ala Ala Tyr
370                 375                 380

Asp Asp Lys Met Asp Ala Asp Gly Arg Val His Asp Pro Glu Arg Ile
385                 390                 395                 400

Ala Tyr Leu His Gly His Leu Arg Ala Val Arg Ala Ile Ala Glu
                405                 410                 415

Gly Ala Asp Val Arg Gly Tyr Tyr Leu Trp Ser Leu Met Asp Asn Phe
                420                 425                 430

Glu Trp Ala Tyr Gly Tyr Gly Lys Arg Phe Gly Ala Val Tyr Val Asp
            435                 440                 445

Tyr Ala Thr Leu Thr Arg Thr Pro Lys Ser Ser Ala His Trp Tyr Gly
450                 455                 460

Gln Ala Ala Lys Thr Gly Ala Leu Pro Pro Leu Ala Pro Ala Pro Ala
465                 470                 475                 480
```

<210> SEQ ID NO 5
<211> LENGTH: 14
<212> TYPE: DNA
<213> ORGANISM: Artificial Sequence
<220> FEATURE:
<223> OTHER INFORMATION: cbstxtR-A S. Scabies

<400> SEQUENCE: 5
cgggagcgct ccca                                                    14

<210> SEQ ID NO 6
<211> LENGTH: 14
<212> TYPE: DNA
<213> ORGANISM: Artificial Sequence
<220> FEATURE:
<223> OTHER INFORMATION: cbstxtB S. scabies

<400> SEQUENCE: 6
ggggagcgct ccca                                                    14

<210> SEQ ID NO 7
<211> LENGTH: 14
<212> TYPE: DNA
<213> ORGANISM: Artificial Sequence
<220> FEATURE:
<223> OTHER INFORMATION: cbscebR-E S. Scabies

<400> SEQUENCE: 7
tgggagcgct ccca                                                    14

<210> SEQ ID NO 8
<211> LENGTH: 59
<212> TYPE: DNA

```
<213> ORGANISM: Artificial Sequence
<220> FEATURE:
<223> OTHER INFORMATION: primer

<400> SEQUENCE: 8
gattccacgc cagcgcggta gtgacgggag acgaccatga ttccggggat ccgtcgacc         59

<210> SEQ ID NO 9
<211> LENGTH: 58
<212> TYPE: DNA
<213> ORGANISM: Artificial Sequence
<220> FEATURE:
<223> OTHER INFORMATION: primer

<400> SEQUENCE: 9
caagcgcttc gtcatccagg tcgatctggg tcgcactcat gtaggctgga gctgcttc          58

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctcccacgag tgatgtgttg                                                     20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccgtgtcctt cttcatggtg                                                     20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gtctggcagt tccaggagtc                                                     20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aggtgttcca ccacaggaag                                                     20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ggacatccag acgcagtaca                                                     20
```

```
<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ctcggtgttg agcttctcct                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tggtcgaggt catcaacaag                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tggacctcga tgaccttctc                                              20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
gagcgactgt ccttcatgg                                               19

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cgtcgtccag taccacgag                                               19

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
cggctacttc ccgatggat                                               19

<210> SEQ ID NO 21
<211> LENGTH: 20
<212> TYPE: DNA
<213> ORGANISM: Artificial Sequence
<220> FEATURE:
<223> OTHER INFORMATION: primer
```

```
<400> SEQUENCE: 21
ctcgatgtca ctcctggtca                                               20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ggatgcgatc cacttctgat                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cgcaccgata tgttgtgttc                                               20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctgggttacg tcccgaacac                                               20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ccttgaggat gtcggagaag                                               20

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
aaatctagac cagcgtgatc ttggtcttg                                     29

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
aaatctagac cgtgtccttc ttcatggtg                                     29
```

```
<210> SEQ ID NO 28
<211> LENGTH: 59
<212> TYPE: DNA
<213> ORGANISM: Artificial Sequence
<220> FEATURE:
<223> OTHER INFORMATION: primer

<400> SEQUENCE: 28
cgcgccccgt aacccgtcgc gcctatcgtg cgccgggtga ttccggggat ccgtcgacc        59

<210> SEQ ID NO 29
<211> LENGTH: 58
<212> TYPE: DNA
<213> ORGANISM: Artificial Sequence
<220> FEATURE:
<223> OTHER INFORMATION: primer

<400> SEQUENCE: 29
ccacgcgggg atgttgtgtg tgccgcaccg gcccggtcat gtaggctgga gctgcttc         58

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
acttcttctg gcccttcgtg                                                   20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gcgggctcct acgactactg                                                   20

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
catatggtga caggccacgg ggc                                               23

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
gaattcggaa gaatcccgcc ccacc                                             25

<210> SEQ ID NO 34
<211> LENGTH: 34
<212> TYPE: DNA
<213> ORGANISM: Artificial Sequence
<220> FEATURE:
<223> OTHER INFORMATION: primer
```

```
<400> SEQUENCE: 34
tgtcaataag cgggagcgct cccacagcgc tctc                               34

<210> SEQ ID NO 35
<211> LENGTH: 34
<212> TYPE: DNA
<213> ORGANISM: Artificial Sequence
<220> FEATURE:
<223> OTHER INFORMATION: primer

<400> SEQUENCE: 35
gagagcgctg tgggagcgct cccgcttatt gaca                               34

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
ccaggtactg tgggagcgct cccacgagtg atgt                               34

<210> SEQ ID NO 37
<211> LENGTH: 34
<212> TYPE: DNA
<213> ORGANISM: Artificial Sequence
<220> FEATURE:
<223> OTHER INFORMATION: primer

<400> SEQUENCE: 37
acatcactcg tgggagcgct cccacagtac ctgg                               34

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
ctcccccagg gggagcgctc ccactgcgct gta                                33

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
tacagcgcag tgggagcgct cccctgggg gag                                 33

<210> SEQ ID NO 40
<211> LENGTH: 34
<212> TYPE: DNA
<213> ORGANISM: Artificial Sequence
<220> FEATURE:
<223> OTHER INFORMATION: primer

<400> SEQUENCE: 40
ggttcaggca tggaagcgct cccattggtg gtcg                               34
```

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
cgaccaccaa tgggagcgct tccatgcctg aacc            34

<210> SEQ ID NO 42
<211> LENGTH: 1369
<212> TYPE: DNA
<213> ORGANISM: Artificial Sequence
<220> FEATURE:
<223> OTHER INFORMATION: Apramycin resistance gene deletion cassette

<400> SEQUENCE: 42
attccgggga tccgtcgacc tgcagttcga agttcctatt ctctagaaag tataggaact     60
tcgaagttcc cgccagcctc gcagagcagg attcccgttg agcaccgcca ggtgcgaata    120
agggacagtg aagaaggaac cccgctcgcg ggtgggcct acttcaccta tcctgcccgg    180
ctgacgccgt tggatacacc aaggaaagtc tacacgaacc cttttggcaaa atcctgtata    240 tcgtgcgaaa aaggatggat ataccgaaaa aatcgctata atgaccccga agcagggtta    300
tgcagcggaa aatgcagctc acggtaactg atgccgtatt tgcagtacca gcgtacggcc    360
cacagaatga tgtcacgctg aaaatgccgg cctttgaatg ggttcatgtg cagctccatc    420
agcaaaaggg gatgataagt ttatcaccac cgactatttg caacagtgcc gttgatcgtg    480
ctatgatcga ctgatgtcat cagcggtgga gtgcaatgtc gtgcaatacg aatggcgaaa    540
agccgagctc atcggtcagc ttctcaacct tgggggttacc cccggcggtg tgctgctggt    600
ccacagctcc ttccgtagcg tccggcccct cgaagatggg ccacttggac tgatcgaggc    660
cctgcgtgct gcgctgggtc cgggagggac gctcgtcatg ccctcgtggt caggtctgga    720
cgacgagccg ttcgatcctg ccacgtcgcc cgttacaccg gaccttggag ttgtctctga    780
cacattctgg cgcctgccaa atgtaaagcg cagcgcccat ccatttgcct ttgcggcagc    840
ggggccacag gcagagcaga tcatctctga tccattgccc ctgccacctc actcgcctgc    900
aagcccggtc gcccgtgtcc atgaactcga tgggcaggta cttctcctcg gcgtgggaca    960
cgatgccaac acgacgctgc atcttgccga gttgatggca aaggttccct atggggtgcc   1020
gagacactgc accattcttc aggatggcaa gttggtacgc gtcgattatc tcgagaatga   1080
ccactgctgt gagcgctttg ccttggcgga caggtggctc aaggagaaga gccttcagaa   1140
ggaaggtcca gtcggtcatg cctttgctcg gttgatccgc tcccgcgaca ttgtggcgac   1200
agccctgggt caactgggcc gagatccgtt gatcttcctg catccgccag aggcgggatg   1260
cgaagaatgc gatgccgctc gccagtcgat tggctgagct cataagttcc tattccgaag   1320
ttcctattct ctagaaagta taggaacttc gaagcagctc agcctaca                1369

<210> SEQ ID NO 43
<211> LENGTH: 14
<212> TYPE: DNA
<213> ORGANISM: Artificial Sequence
<220> FEATURE:
<223> OTHER INFORMATION: Nucleotide sequence cbsbglC

<400> SEQUENCE: 43
tggaagcgct ccca            14